US006375952B1

(12) United States Patent
Koelle et al.

(10) Patent No.: US 6,375,952 B1
(45) Date of Patent: Apr. 23, 2002

(54) IMMUNOLOGICAL HERPES SIMPLEX VIRUS ANTIGENS AND METHODS FOR USE THEREOF

(75) Inventors: David M. Koelle; Lawrence Corey, both of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/368,770

(22) Filed: Aug. 5, 1999

Related U.S. Application Data

(60) Provisional application No. 60/095,724, filed on Aug. 7, 1998, and provisional application No. 60/095,723, filed on Aug. 7, 1998.

(51) Int. Cl.[7] .................... A61K 39/245; A61K 39/275; C12N 15/38; C12N 15/62; C07K 14/03

(52) U.S. Cl. ................. 424/186.1; 424/192.1; 424/199.1; 424/231.1; 536/23.4; 536/23.7; 530/350; 435/69.3; 435/69.7; 435/235.1; 435/252.3; 435/320.1; 435/325

(58) Field of Search ............................ 424/186.1, 231.1, 424/192.1, 199.1; 435/235.1, 69.1, 69.3, 195, 196, 69.7, 325, 252.3; 536/23.4, 23.72; 530/350

(56) References Cited

U.S. PATENT DOCUMENTS

| 4,859,587 A | 8/1989 | Roizman |
| 5,632,992 A | 5/1997 | Nesburn et al. |
| 5,714,152 A | 2/1998 | Burke et al. |

FOREIGN PATENT DOCUMENTS

| WO | WO 92/02251 | 2/1992 |
| WO | WO 95/16779 | 6/1995 |
| WO | WO 97/05265 | 2/1997 |

OTHER PUBLICATIONS

Roisman et al. Herpes Simplex Viruses and Their Replication. In: Fundamental Virology, 2nd Edition, ed. Fields et al, Raven Press, New York, p. 849–895, 1991.*

Tatman, J.D. et al., "Assembly of Herpes Simplex Virus Type 1 Using a Panel of Recombinant Baculoviruses," Journal of General Virology, (1994), 75, 1101–1113.

M.A. Tigges et al.(1992) Human CD8+ Herpes Simplex Virus–Specific Cytotoxic T–Lymphocyte Clones Recognize Diverse Virion Protein Antigens, Journal of Virology, 66(3):1622–1634.

C.M. Posavad et al. (1996) High Frequency of CD8+ Cytotoxic T–Lymphoctye Precursors Specific for Herpes Simplex Viruses in Persons with Genital Herpes, Journal of Virology 70(11):8165–8168.

D.M. Koelle et al. (1998) Clearance of HSV–2 from Recurrent Genital Lesions Correlates with Infiltration of HSV–Specific Cytotoxic T Lymphoctyes, The Journal of Clinical Investigation 101(7):1500–1508.

D.M. Koelle et al. (1997) Preferrential Presentation of Herpes Simplex Virus T–Cell Antigen by HLA DQA1*0501/DQB1*0201 in Comparison to HLA DQA1*0201/DQB1*0201, Human Immunology 53(2):195–205.

S. Reichstetter et al. (1999) MCH–Peptide Ligand Interactions Establish a Functional Threshold for Antigen–Specific T Cell Recognition, Human Immunology 60(7):608–618.

W.W. Kwok et al. (1999) Peptide Binding Affinity and pH Variation Establish Functional Thresholds for Activation of HLA–DQ–Restricted T Cell Recognition, Human Immunology 60(7):619–626.

D.M. Koelle et al. (1994) Direct Recovery of Herpes Simplex Virus (HSV)–Specific T Lymphocyte Clones from Recurrent Genital HSV–2 Lesions, The Journal of Infectious Diseases 169:956–61.

D.M. Koelle et al. (1994) Antigenic Specificities of Human CD+ T–Cell Clones Recovered from Recurrent Genital Herpes Simples Virus Type 2 Lesions, Journal of Virology 68(5):2803–2810.

A. Dolan et al. (1998) The Genome Sequence of Herpes Simplex Virus Type 2, Journal of Virology 72(3):2010–2021.

G. Elliott and P. O'Hare (1997) Intercellular Trafficking and Protein Delivery by a Herpesvirus Structural Protein, Cell 88:223–233.

E. De Plaen et al. (1997) Cloning of Genes Coding for Antigens Recognized by Cytolytic T Lymphocytes, Immunology Methods Manual 692–718.

D.M. Koelle, (1995) The Roles of T Lymphocytes in Host Responses to Herpes Simplex Virus, Herpes, 2:83–88.

Bjornberg et al. Protein Expression and Purification 4:149–159, 1993.*

Williams et al. Virology 156:282–292, 1987.*

Williams. Journal of Biological Chemistry 259(16):10080–10084, 1984.*

Koelle et al. Journal of Virology 72(9):7476–7483, Sep. 1998.*

* cited by examiner

Primary Examiner—Mary E. Mosher
(74) Attorney, Agent, or Firm—Gates & Cooper LLP

(57) ABSTRACT

The invention provides HSV antigens that are useful for the prevention and treatment of HSV infection. Disclosed herein are antigens and/or their constituent epitopes confirmed to be recognized by T-cells derived from herpetic lesions or from uterine cervix. T-cells having specificity for antigens of the invention have demonstrated cytotoxic activity against cells loaded with virally-encoded peptide epitopes, and in many cases, against cells infected with HSV. The identification of immunogenic antigens responsible for T-cell specificity provides improved anti-viral therapeutic and prophylactic strategies. Compositions containing antigens or polynucleotides encoding antigens of the invention provide effectively targeted vaccines for prevention and treatment of HSV infection.

39 Claims, 5 Drawing Sheets

SEQUENCE LISTING

<160> NUMBER OF SEQ ID NOS: 11

<210> SEQ ID NO 1
<211> LENGTH: 20
<212> TYPE: DNA
<213> ORGANISM: herpes simplex virus

<400> SEQUENCE: 1
catggctgaa tatcgacggt                                                    20

<210> SEQ ID NO 2
<211> LENGTH: 22
<212> TYPE: DNA
<213> ORGANISM: herpes simplex virus

<400> SEQUENCE: 2
ctagagccgg atcgatccgg tc                                                 22

<210> SEQ ID NO 3
<211> LENGTH: 22
<212> TYPE: PRT
<213> ORGANISM: herpes simplex virus

<400> SEQUENCE: 3

Gly Gly Pro Val Gly Ala Gly Gly Arg Ser His Ala Pro Pro Ala rg
 1               5                  10                  15

Thr Pro Lys Met Thr Arg
            20

<210> SEQ ID NO 4
<211> LENGTH: 28
<212> TYPE: DNA
<213> ORGANISM: herpes simplex virus

<400> SEQUENCE: 4
ggaagatcta cctctcgccg ctccgtca                                           28

<210> SEQ ID NO 5
<211> LENGTH: 29
<212> TYPE: DNA
<213> ORGANISM: herpes simplex virus

<400> SEQUENCE: 5
ccggaattct tgtctgtcgt ctgaacgcg                                          29

<210> SEQ ID NO 6
<211> LENGTH: 28
<212> TYPE: DNA
<213> ORGANISM: herpes simplex virus

<400> SEQUENCE: 6
taaggtacct atgagtcagt gggggccc                                           28

<210> SEQ ID NO 7
<211> LENGTH: 27
<212> TYPE: DNA
<213> ORGANISM: herpes simplex virus

<400> SEQUENCE: 7
aaactgcagg aggcgcggtc tagatgc                                            27

```
<210> SEQ ID NO 8
<211> LENGTH: 30
<212> TYPE: DNA
<213> ORGANISM: herpes simplex virus

<400> SEQUENCE: 8
ctgggatcca tggagctcag ctatgccacc                                    30

<210> SEQ ID NO 9
<211> LENGTH: 30
<212> TYPE: DNA
<213> ORGANISM: herpes simplex virus

<400> SEQUENCE: 9
cgcgaattct cacacagact ggccgtgctg                                    30

<210> SEQ ID NO 10
<211> LENGTH: 31
<212> TYPE: DNA
<213> ORGANISM: herpes simplex virus

<400> SEQUENCE: 10
cggggtacct gctcgcgggg ccgggttggt g                                  31

<210> SEQ ID NO 11
<211> LENGTH: 30
<212> TYPE: DNA
<213> ORGANISM: herpes simplex virus

<400> SEQUENCE: 11
tgctctagag ccttaccagc ggacggacgg                                    30
```

Immunological Herpes Simplex Virus Antigens and Methods for Use Thereof

This application claims the benefit of U.S. provisional patent applications 60/095,723 and 60/095,724, both filed on Aug. 7, 1998, the entire contents of which are incorporated herein by reference.

The invention disclosed herein was made with Government support under Grant No. AI34616, awarded by the National Institutes of Health. The government has certain rights in this invention.

Throughout this application various publications are referenced. The disclosures of these publications in their entireties are hereby incorporated by reference into this application in order to describe more fully the state of the art to which this invention pertains.

TECHNICAL FIELD OF THE INVENTION

The invention relates to molecules, compositions and methods that can be used for the treatment and prevention of herpes simplex virus (HSV) infection. More particularly, the invention identifies epitopes of HSV proteins that can be used for the development of methods, molecules and compositions that stimulate or augment HSV-specific immunity.

BACKGROUND OF THE INVENTION

The complete, known DNA sequence of HSV types 1 and 2 are approximately 160 kb and encodes about 85 genes, each of which encodes at least one protein. Unknown are the immunological epitopes within these proteins, each epitope approximately 9–12 amino acids in length, that are capable of eliciting an effective T cell immune response to viral infection. Cellular immune responses are required to limit the severity of recurrent HSV infection in humans. HSV-specific CD4 T cells can be cytotoxic towards virally-infected cells (M. Yasukawa et a., 1991, J. Immunol., 146:1341–1347; M. Yasukawa et al., 1984, J. Immunol., 133:2736–42). HSV-specific T cells can also reduce the titer of HSV replication in HSV-infected, HLA-matched cells, produce lymphokines with antiviral or immunomodulatory activity, or provide specific B cell help to augment antiviral antibody responses. References relating to the antigenic specificity of HSV-specific T cells include: A. G. Langenberg et al., 1995, Ann. Int. Med. 122:889–898; A. Mikloska et al., 1998, J. Gen. Virol., 79:353–361; J. W. Torseth et al., 1987, J. Virol., 61:1532–1539; M. Yasukawa et al., 1985, J. Immunol., 134:2679–2687.

There remains a need to identify specific epitopes capable of eliciting an effective immune response to HSV infection. Such information can lead to the identification of more effective immunogenic antigens useful for the prevention and treatment of HSV infection.

SUMMARY OF THE INVENTION

The invention provides HSV antigens, polypeptides comprising HSV antigens, polynucleotides encoding the polypeptides, vectors, and recombinant viruses containing the polynucleotides, antigen-presenting cells (APCs) presenting the polypeptides, immune cells directed against HSV, and pharmaceutical compositions. The pharmaceutical compositions can be used both prophylactically and therapeutically. The antigens of the invention are recognized by T cells recovered from herpetic lesions. The invention additionally provides methods, including methods for preventing and treating HSV infection, for killing HSV-infected cells, for inhibiting viral replication, for enhancing secretion of antiviral and/or immunomodulatory lymphokines, and for enhancing production of HSV-specific antibody. For preventing and treating HSV infection, for enhancing secretion of antiviral and/or immunomodulatory lymphokines, for enhancing production of HSV-specific antibody, and generally for stimulating and/or augmenting HSV-specific immunity, the method comprises administering to a subject a polypeptide, polynucleotide, recombinant virus, APC, immune cell or composition of the invention. The methods for killing HSV-infected cells and for inhibiting viral replication comprise contacting an HSV-infected cell with an immune cell of the invention. The immune cell of the invention is one that has been stimulated by an antigen of the invention or by an APC that presents an antigen of the invention. A method for producing such immune cells is also provided by the invention. The method comprises contacting an immune cell with an APC, preferably a dendritic cell, that has been modified to present an antigen of the invention. In a preferred embodiment, the immune cell is a T cell such as a CD4+ or CD8+ T cell.

In one embodiment, the invention provides a composition comprising an HSV polypeptide. The polypeptide can comprise a $U_L19$, $U_L21$, $U_L49$ or $U_L50$ protein or a fragment thereof, or a polypeptide selected from the group consisting of: amino acids 1078–1319 of $U_L19$; amino acids 148–181 of $U_L21$; amino acids 105–190 or 177–220 of $U_L49$; amino acids 118–312 of U acids 1–273 of glycoprotein E (gE); amino acids 185–197, 209–221 or 430–449 of VP16; and substitutional variants of the above. Also provided is an isolated polynucleotide that encodes a polypeptide of the invention, and a composition comprising the polynucleotide. The invention additionally provides a recombinant virus genetically modified to express a polynucleotide of the invention, and a composition comprising the recombinant virus. In preferred embodiments, the virus is a vaccinia virus, canary pox virus, HSV, lentivirus, retrovirus or adenovirus. A composition of the invention can be a pharmaceutical composition. The composition can optionally comprise a pharmaceutically acceptable carrier and/or an adjuvant.

The invention additionally provides a method of identifying an immunogenic epitope of an infectious organism, such as a virus, bacteria or parasite. In one embodiment, the method comprises preparing a collection of random fragments of the organismal genome. The method further comprises expressing a polypeptide encoded by a fragment of the collection, and recovering the expressed polypeptide. Preferably, the polypeptide is expressed as an insoluble inclusion body. In one embodiment, the polypeptide is expressed as a fusion protein using, for example, a pUEX vector to express an insoluble β-galactosidase fusion protein. The ability of the expressed polypeptide to elicit a cellular immune response is then assayed. Ability to elicit a cellular immune response is indicative of the presence of an immunogenic epitope.

The above steps can be repeated with subfragments of the genome fragments. The method can further comprise sequencing a fragment of the genome. In one embodiment, the assaying comprises performing a T cell proliferation assay. The assaying can be performed with an immune cell derived from a subject that has been exposed to the infectious organism. In preferred embodiments, the cell is derived from a site of active infection, such as skin or cervix, or from blood of an infected subject.

The invention further provides immunogenic epitopes identified by the method of the invention, polypeptides comprising the epitopes, and polynucleotides encoding the polypeptides. Suitable infectious organisms include bacteria, parasites and viruses. Examples of viruses include DNA and RNA viruses, both double-stranded and single-stranded. The method of the invention provides a strategy for combating a variety of infectious organisms, including those which exhibit significant variability, as knowledge of the organism's nucleic acid sequence is not required.

DETAILED DESCRIPTION OF THE INVENTION

Figure 1A:
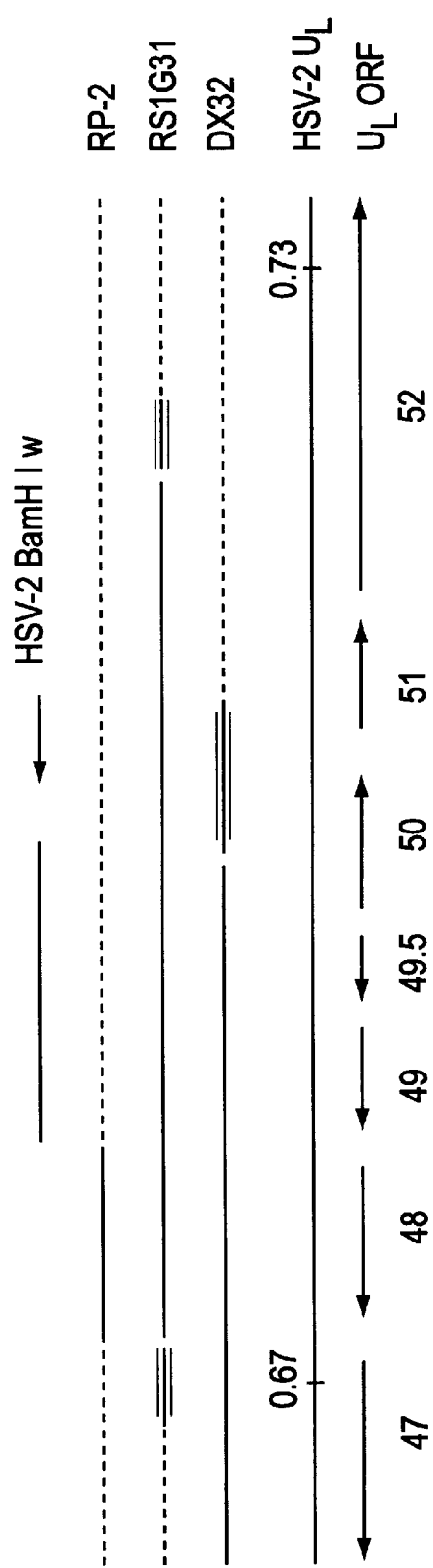
FIG. 1A is a schematic representing organization of the HSV genome in the region of 0.67–0.73 map units. Boundaries are approximate. HSV-1×HSV-2 intertypic recombinant viruses (IRV) are also shown. HSV-2 DNA is indicated by a solid line; HSV-1 DNA by a dashed line, and indeterminate regions by a multiple line. The HSV-2 BamH I w fragment used for expression cloning is also shown.

The invention provides HSV antigens that are useful for the prevention and treatment of HSV infection. Disclosed herein are antigens and/or their constituent epitopes confirmed to be recognized by T-cells derived from herpetic lesions. In some embodiments, T-cells having specificity for antigens of the invention have demonstrated cytotoxic activity against virally-infected cells. The identification of immunogenic antigens responsible for T-cell specificity facilitates the development of improved anti-viral therapeutic and prophylactic strategies. Compositions containing antigens or polynucleotides encoding antigens of the invention provide effectively targeted vaccines for prevention and treatment of HSV infection.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 8 amino acids.

As used herein, "HSV polypeptide" includes HSV-1 and HSV-2, unless otherwise indicated. References to amino acids of HSV proteins or polypeptides are based on the genomic sequence information regarding HSV-2 as described in A. Dolan et al., 1998, J. Virol. 72(3):2010–2021.

As used herein, "substitutional variant" refers to a molecule having one or more amino acid substitutions or deletions in the indicated amino acid sequence, yet retaining the ability to be recognized by an immune cell. One method for determining whether a molecule can be recognized by an immune cell is the proliferation assay described in D. M. Koelle et al., 1994, J. Virol. 68(5):2803–2810.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells. As used herein, each of these cell types and each of their progenitors is referred to as a "dendritic cell," unless otherwise specified.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, Remington's Pharmaceutical Sciences, Chapter 43, 14th Ed., Mack Publishing Co, Easton Pa. 18042, USA).

As used herein, "adjuvant" includes those adjuvants commonly used in the art to facilitate the stimulation of an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); QS-21 (Aquilla); MPL or 3d-MPL (Ribi ImmunoChem Research, Inc., Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

HSV Polypeptides

In one embodiment, the invention provides an isolated herpes simplex virus (HSV) polypeptide, wherein the polypeptide comprises a $U_L19$ (major capsid antigen, VP5), $U_L21$, $U_L49$ (VP22) or $U_L50$ protein or a fragment thereof In another embodiment, the invention provides an isolated HSV polypeptide selected from the group consisting of: amino acids 1078–1319 of $U_L19$; amino acids 148–181 of $U_L21$; amino acids 105–190 or 177–220 of $U_L49$; amino acids 118–312 of $U_L50$; amino acids 1–273 of glycoprotein E (gE; US8); amino acids 185–197, 209–221 or 430–449 of VP16; and substitutional variants of the above polypeptides. The references to amino acid residues are made with respect to the proteins of the HSV-2 genome as described in A. Dolan et al., 1998, J. Virol. 72(3):2010–2021.

The polypeptide can be a fusion protein. In one embodiment, the fusion protein is soluble. A soluble fusion protein of the invention can be suitable for injection into a subject and for eliciting an immune response. Within certain embodiments, a polypeptide can be a fusion protein that comprises multiple polypeptides as described herein, or that comprises at least one polypeptide as described herein and an unrelated sequence. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., 1985, Gene 40:39–46; Murphy et al., 1986, Proc. Natl. Acad. Sci. USA 83:8258–8262; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al., 1997, New Engl. J. Med., 336:869).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In some embodiments, it may be desirable to couple a therapeutic agent and a polypeptide of the invention, or to couple more than one polypeptide of the invention. For example, more than one agent or polypeptide may be coupled directly to a first polypeptide of the invention, or linkers that provide multiple sites for attachment can be used. Alternatively, a carrier can be used. Some molecules are particularly suitable for intercellular trafficking and protein delivery, including, but not limited to, VP22 Elliott and O'Hare, 1997, Cell 88:223–233; see also Kim et al., 1997, J. Immunol. 159:1666–1668; Rojas et al., 1998, Nature Biotechnology 16:370; Kato et al., 1998, FEBS Lett. 427(2):203–208; Vives et al., 1997, J. Biol. Chem. 272(25):16010–7; Nagahara et al., 1998, Nature Med. 4(12):1449–1452).

A carrier may bear the agents or polypeptides in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not part of the natural environment.

The polypeptide can be isolated from its naturally-occurring form, produced by recombinant means or synthesized chemically. Recombinant polypeptides encoded by DNA sequences described herein can be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably the host cells employed are *E. coli,* yeast or a mammalian cell line such as COS or CHO. Supernatants from the soluble host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Fragments and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain Merrifield, 1963, J. Am. Chem. Soc. 85:2146–2149). Equipment for automated synthesis of polypeptides is commercially available from suppliers such as Perkin Elmer/Applied BioSystems Division (Foster City, Calif.), and may be operated according to the manufacturer's instructions.

Variants of the polypeptide for use in accordance with the invention can have one or more amino acid substitutions, deletions, additions and/or insertions in the amino acid sequence indicated that result in a polypeptide that retains the ability to elicit an immune response to HSV or HSV-infected cells. Such variants may generally be identified by modifying one of the polypeptide sequences described herein and evaluating the reactivity of the modified polypeptide using a known assay such as a T cell assay described herein. Polypeptide variants preferably exhibit at least about 70%, more preferably at least about 90%, and most preferably at least about 95% identity to the identified polypeptides. These amino acid substitutions include, but are not necessarily limited to, amino acid substitutions known in the art as "conservative".

A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polynucleotides, Vectors, Host Cells and Recombinant Viruses

The invention provides polynucleotides that encode one or more polypeptides of the invention. The polynucleotide can be included in a vector. The vector can further comprise an expression control sequence operably linked to the polynucleotide of the invention. In some embodiments, the vector includes one or more polynucleotides encoding other molecules of interest. In one embodiment, the polynucleotide of the invention and an additional polynucleotide can be linked so as to encode a fusion protein.

Within certain embodiments, polynucleotides may be formulated so to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

The invention also provides a host cell transformed with a vector of the invention. The transformed host cell can be used in a method of producing a polypeptide of the invention. The method comprises culturing the host cell and recovering the polypeptide so produced. The recovered polypeptide can be purified from culture supernatant.

Vectors of the invention can be used to genetically modify a cell, either in vivo, ex vivo or in vitro. Several ways of genetically modifying cells are known, including transduction or infection with a viral vector either directly or via a retroviral producer cell, calcium phosphate precipitation, fusion of the recipient cells with bacterial protoplasts containing the DNA, treatment of the recipient cells with liposomes or microspheres containing the DNA, DEAE dextran, receptor-mediated endocytosis, electroporation, micro-injection, and many other techniques known to those of skill. See, e.g., Sambrook et al. Molecular Cloning—A Laboratory Manual (2nd ed.) 1–3, 1989; and Current Protocols in Molecular Biology, F. M. Ausubel et al., eds., Greene Publishing Associates, Inc. and John Wiley & Sons, Inc., (1994 Supplement).

Examples of viral vectors include, but are not limited to retroviral vectors based on, e.g., HIV, SIV, murine retroviruses, gibbon ape leukemia virus and other viruses such as adeno-associated viruses (AAVs) and adenoviruses. (Miller et al. 1990, Mol. Cell Biol. 10:4239; J. Kolberg 1992, NIH Res. 4:43, and Cornetta et al. 1991, Hum. Gene Ther. 2:215). Widely used retroviral vectors include those based upon murine leukemia virus MuLV), gibbon ape leukemia virus (GaLV), ecotropic retroviruses, simian immunodeficiency virus (SIV), human immunodeficiency virus (HIV), and combinations. See, e.g. Buchscher et al. 1992, J. Virol. 66(5):2731–2739; Johann et al. 1992, J. Virol. 66(5):1635–1640; Sommerfelt et al. 1990, Virol. 176:58–59; Wilson et al. J. Virol. 63:2374–2378; Miller et al. 1991, J. Virol. 65:2220–2224, and Rosenberg and Fauci 1993 in Fundamental Immunology, Third Edition, W. E. Paul (ed.) Raven Press, Ltd., New York and the references therein; Miller et al. 1990, Mol. Cell. Biol. 10:4239; R. Kolberg 1992, J. NIH Res. 4:43; and Cornetta et al. 1991, Hum. Gene Ther. 2:215.

In vitro amplification techniques suitable for amplifying sequences to be subcloned into an expression vector are known. Examples of such in vitro amplification methods, including the polymerase chain reaction (PCR), ligase chain reaction (LCR), Qβ-replicase amplification and other RNA polymerase mediated techniques (e.g., NASBA), are found in Sambrook et al. 1989, Molecular Cloning—A Laboratory Manual (2nd Ed) 1–3; and U.S. Pat. No. 4,683,202; PCR Protocols A Guide to Methods and Applications (Innis et al. eds.) Academic Press Inc. San Diego, Calif. 1990. Improved methods of cloning in vitro amplified nucleic acids are described in U.S. Pat. No. 5,426,039.

The invention additionally provides a recombinant microorganism genetically modified to express a polynucleotide of the invention. The recombinant microorganism can be useful as a vaccine, and can be prepared using techniques known in the art for the preparation of live attenuated vaccines. Examples of microorganisms for use as live vaccines include, but are not limited to, viruses and bacteria. In a preferred embodiment, the recombinant microorganism is a virus. Examples of suitable viruses include, but are not limited to, vaccinia virus, canary pox virus, retrovirus, lentivirus, HSV and adenovirus.

Compositions

The invention provides compositions that are useful for treating and preventing HSV infection. The compositions can be used to inhibit viral replication and to kill virally-infected cells. In one embodiment, the composition is a pharmaceutical composition. The composition can comprise a therapeutically or prophylactically effective amount of a polypeptide, polynucleotide, recombinant virus, APC or immune cell of the invention. An effective amount is an amount sufficient to elicit or augment an immune response, e.g., by activating T cells. One measure of the activation of T cells is a proliferation assay, as described in D. M. Koelle et al., 1994, J. Virol. 68(5):2803–2810. In some embodiments, the composition is a vaccine.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

The composition of the invention can further comprise one or more adjuvants. Examples of adjuvants include, but are not limited to, helper peptide, alum, Freund's, muramyl tripeptide phosphatidyl ethanolamine or an immunostimulating complex, including cytokines. In some embodiments, such as with the use of a polynucleotide vaccine, an adjuvant such as a helper peptide or cytokine can be provided via a polynucleotide encoding the adjuvant. Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other viral antigens may be present, either incorporated into a fusion polypeptide or as a separate compound, within the composition or vaccine.

A pharmaceutical composition or vaccine may contain DNA encoding one or more of the polypeptides of the invention, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143–198, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317–321; Flexner et al., 1989, Ann. My Acad. Sci. 569:86–103; Flexner et al., 1990, Vaccine 8:17–21; U.S. Pat. Nos. 4,603,112, 4,769,330, and 5,017,487; WO 89/01973; U.S. Pat. No. 4,777,127; GB 2,200,651; EP 0,345,242; WO 91102805; Berkner, 1988, Biotechniques 6:616–627; Rosenfeld et al., 1991, Science 252:431–434; Kolls et al., 1994, Proc. Natl. Acad. Sci. USA 91:215–219; Kass-Eisler et al., 1993, Proc. Natl. Acad. Sci. USA 90:11498–11502; Guzman et al., 1993, Circulation 88:2838–2848; and Guzman et al., 1993, Cir. Res. 73:1202–1207. Techniques for incorporating DNA into such expression systems are well known to those of ordinary skill in the art. The DNA may also be "naked," as described, for example, in Ulmer et al., 1993, Science 259:1745–1749 and reviewed by Cohen, 1993, Science 259:1691–1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145–173.

Preferred adjuvants for use in eliciting a predominantly Th1-type response include, for example, a combination of monophosphoryl lipid A, preferably 3de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

The compositions described herein may be administered as part of a sustained release formulation (i.e. a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets HSV-infected cells. Delivery vehicles include antigen presenting cells (APCs), such as dendritic cells, macrophages, B cells, monocytes and other cells that may be engineered to be efficient APCs.

Such cells may, but need not, be genetically modified to increase the capacity for presenting the antigen, to improve activation and/or maintenance of the T cell response, to have antiviral effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic immunity (see Timmerman and Levy, Ann. Rev. Med. 50:507–529, 1999). In general, dendritic cells may be identified based on their typical shape (stellate in situ, with marked cytoplasmic processes (dendrites) visible in vitro) and based on the a lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998, Nature Med. 4:594–600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-C SF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86). APCs may generally be transfected with a polynucleotide encoding a polypeptide (or portion or other variant thereof such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, Immunology and Cell Biology 75:456–460. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Administration of the Compositions

Treatment includes prophylaxis and therapy. Prophylaxis or treatment can be accomplished by a single direct injection at a single time point or multiple time points. Administration can also be nearly simultaneous to multiple sites.

Patients or subjects include mammals, such as human, bovine, equine, canine, feline, porcine, and ovine animals.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as HSV infection, the physician needs to evaluate the production of an immune response against the virus, progression of the disease, and any treatment-related toxicity.

For example, a vaccine or other composition containing a subunit HSV protein can include 1–10,000 micrograms of HSV protein per dose. In a preferred embodiment, 10–1000 micrograms of HSV protein is included in each dose in a more preferred embodiment 10–100 micrograms of HSV protein dose. Preferably, a dosage is selected such that a single dose will suffice or, alternatively, several doses are administered over the course of several months. For compositions containing HSV polynucleotides or peptides, similar quantities are administered per dose.

In one embodiment, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an antiviral immune response, and is at least 10–50% above the basal (i.e., untreated) level. Such vaccines should also be capable of causing an immune response that leads to an improved clinical outcome in vaccinated patients as compared to non-vaccinated patients. In general, for pharmaceutical compositions and vaccines comprising one or more polypeptides, the amount of each polypeptide present in a dose ranges from about 100 μg to 5 mg per kg of host. Preferably, the amount ranges from about 10 to about 1000 μg per dose. Suitable volumes for administration will vary with the size, age and immune status of the patient, but will typically range from about 0.1 mL to about 5 mL, with volumes less than about 1 mL being most common.

Compositions comprising immune cells are preferably prepared from immune cells obtained from the subject to whom the composition will be administered. Alternatively, the immune cells can be prepared from an HLA-compatible donor. The immune cells are obtained from the subject or donor using conventional techniques known in the art, exposed to APCs modified to present an epitope of the invention, expanded ex vivo, and administered to the subject. Protocols for ex vivo therapy are described in Rosenberg et al., 1990, New England J. Med. 9:570–578. In addition, compositions can comprise APCs modified to present an epitope of the invention.

Immune cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to enrich and rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Administration by many of the routes of administration described herein or otherwise known in the art may be accomplished simply by direct administration using a needle, catheter or related device, at a single time point or at multiple time points.

In Vivo Testing of Identified Antigens

Conventional techniques can be used to confirm the in vivo efficacy of the identified HSV antigens. For example, one technique makes use of a mouse challenge model. Those skilled in the art, however, will appreciate that these methods are routine, and that other models can be used.

Once a compound or composition to be tested has been prepared, the mouse or other subject is immunized with a series of injections. For example up to 10 injections can be administered over the course of several months, typically with one to 4 weeks elapsing between doses. Following the last injection of the series, the subject is challenged with a dose of virus established to be a uniformly lethal dose. A control group receives placebo, while the experimental group is actively vaccinated. Alternatively, a study can be designed using sublethal doses. Optionally, a dose-response study can be included. The end points to be measured in this study include death and severe neurological impairment, as evidenced, for example, by spinal cord gait. Survivors can also be sacrificed for quantitative viral cultures of key organs including spinal cord, brain, and the site of injection. The quantity of virus present in ground up tissue samples can be measured. Compositions can also be tested in previously infected animals for reduction in recurrence to confirm efficacy as a therapeutic vaccine.

Efficacy can be determined by calculating the $IC_{50}$, which indicates the micrograms of vaccine per kilogram body weight required for protection of 50% of subjects from death. The $IC_{50}$ will depend on the challenge dose employed. In addition, one can calculate the $LD_{50}$, indicating how many infectious units are required to kill one half of the subjects receiving a particular dose of vaccine. Determination of the post mortem viral titer provides confirmation that viral replication was limited by the immune system.

A subsequent stage of testing would be a vaginal inoculation challenge. For acute protection studies, mice can be used. Because they can be studied for both acute protection and prevention of recurrence, guinea pigs provide a more physiologically relevant subject for extrapolation to humans. In this type of challenge, a nonethal dose is administered, the guinea pig subjects develop lesions that heal and recur. Measures can include both acute disease amelioration and recurrence of lesions. The intervention with vaccine or other composition can be provided before or after the inoculation, depending on whether one wishes to study prevention versus therapy.

Methods

The invention provides a method for treatment and/or prevention of HSV infection in a subject. The method comprises administering to the subject a composition of the invention. The composition can be used as a therapeutic or prophylactic vaccine. In one embodiment, the HSV is HSV-2. Alternatively, the HSV is HSV-1. The invention additionally provides a method for inhibiting HSV replication, for killing HSV-infected cells, for increasing secretion of lymphokines having antiviral and/or immunomodulatory activity, and for enhancing production of herpes-specific antibodies. The method comprises contacting an HSV-infected cell with an immune cell directed against an antigen of the invention, for example, as described in the Examples presented herein. The contacting can be performed in vitro or in vivo. In a preferred embodiment, the immune cell is a T cell. T cells include CD4 and CD8 T cells. Compositions of the invention can also be used as a tolerizing agent against immunopathologic disease, such as eye disease, e.g., herpes keratitis.

In addition, the invention provides a method of producing immune cells directed against HSV. The method comprises contacting an immune cell with an antigen-presenting cell, wherein the antigen-presenting cell is modified to present an antigen included in a polypeptide of the invention. Preferably, the antigen-presenting cell is a dendritic cell. The cell can be modified by, for example, peptide loading or genetic modification with a nucleic acid sequence encoding the polypeptide. In one embodiment, the immune cell is a T cell. T cells include CD4 and CD8 T cells. Also provided are immune cells produced by the method. The immune cells can be used to inhibit HSV replication, to kill HSV-infected cells, in vitro or in vivo, to increase secretion of lymphokines having antiviral and/or immunomodulatory activity, to enhance production of herpes-specific antibodies, or in the treatment or prevention of HSV infection in a subject.

The invention provides methods for identifying immunogenic epitopes associated with infectious organisms. In one embodiment, the method comprises preparing a collection of random fragments of the organismal genome. The preparing can comprise digesting the entire genome, although it is not necessary to begin with the full genome. The digesting preferably comprises contacting the genome with one or more restriction enzymes to obtain a collection of random fragments having a desired range of lengths. Alternatively, one can sonicate, nebulize or otherwise treat material containing the genome of interest and isolate from a gel fragments of an appropriate size.

The digesting, and the selection of restriction enzymes, is designed to obtain fragments of the genome that are longer than the average length of a T cell epitope, e.g., greater than about 30 nucleotides in length. Preferably, the fragments are small enough such that genetic stops are infrequent, e.g., about 200 to about 500 base pairs in length. Where the genomic sequence or a restriction map of an organism of interest is known, one can analyze the genome to identify restriction sites that, if targeted with the appropriate restriction enzymes, will result in the desired number of fragments of an appropriate length. The restriction enzymes can also be selected to target sites that are compatible with sites in a cloning vector to be used.

The random fragments can then be used to express polypeptides encoded by the fragments. The fragments can be expressed individually, or preferably, as a pool of polypeptides, either alone or as fusion proteins. Those skilled in the art will appreciate that polypeptides can be expressed from either DNA or RNA as a starting material. For example, expression of polypeptides from RNA viruses can be achieved by first preparing a cDNA from the RNA fragment, and then using the cDNA to express the polypeptide. Preferably, the polypeptide is expressed as an insoluble inclusion body. Expressing the polypeptide as an insoluble inclusion body permits the expression of a large quantity of polypeptide in a form that is readily processed and presented by APCs. Proteins expressed as inclusion bodies are easy to purify, provide a highly efficient method for expression and processing and facilitate application of the method to unsequenced organisms.

The polypeptide can be expressed from a vector containing the fragment of genome. In a preferred embodiment, the vector is a plasmid, such as a pUEX vector. Those skilled in the art will appreciate that other vectors can be used that are capable of expressing polypeptide from an insert. Preferably, the polypeptide is expressed as a fusion protein. One example of a preferred fusion protein is an insoluble β-galactosidase fusion protein. In one embodiment, the expressing comprises culturing a host cell transformed with a vector containing the fragment of genome. In a preferred embodiment of the method, fragments are ligated into expression vectors in the three different reading frames, and in both directions.

The method further comprises recovering the expressed polypeptides. For example, polypeptide expressed by a cultured host cell can be recovered by collecting supernatant from the cultured host cell. The recovered polypeptide can be further purified from the supernatant using standard techniques. Polypeptide expressed as an insoluble inclusion body can be recovered by, for example, sonication, lysosyme and detergent-assisted isolation of insoluble inclusion bodies as described in Neophytou et al., 1996, Proc. Natl. Acad. Sci. USA, 93:2014–2018.

The method further comprises assaying the ability of the expressed polypeptide to elicit an immune response. The ability to elicit an immune response is indicative of the presence of an immunogenic epitope within the polypeptide. In one embodiment, the immune response is a cellular immune response. The assaying can comprise performing an assay that measures T cell stimulation or activation. Examples of T cells include CD4 and CD8 T cells.

One example of a T cell stimulation assay is a T cell proliferation assay, such as that described in Example 1 below or in D. M. Koelle et al., 1994, J. Virol. 68(5):2803–2810. The T cell proliferation assay can comprise, for example, contacting the expressed polypeptide with an antigen-presenting cell and a T cell directed against the virus, and measuring T cell proliferation. T cell proliferation can be measured by measuring the incorporation of $^3$H-thymidine or other proliferation marker. The proliferation assay indicates T cell stimulation if increased proliferation is detected in T cells exposed to test antigen as compared to T cell proliferation in response to control antigen. One exemplary criterion for increased proliferation is a statistically significant increase in counts per minute (cpm) based on liquid scintillation counting of $^3$H-thymidine incorporated into precipitated nucleic acid preparations of test as compared to control cell cultures. Another example of assay for T cell stimulation or activation is a cytolysis assay. One example of a cytolysis assay is provided in Example 1, below.

The assay can be performed on pools of polypeptides to identify pools containing active moieties. Further assays can then be performed on increasingly smaller subsets of the original pools to isolate polypeptides of interest. The material containing a fragment of interest, e.g., a plasmid with its viral insert, can be purified and the viral fragment sequenced. Based on the obtained sequence information, synthetic peptides can be prepared for subsequent testing and confirmation of the identified antigens. Sequencing of fragments can also lead to the identification of novel genes.

The foregoing method steps can be repeated, wherein subfragments of the genome fragments are prepared. Increasingly smaller fragments can be expressed and tested to determine the minimal epitope.

The method of the invention can be applied to a variety of infectious organisms, including bacteria, parasites and viruses. Preferred viruses are those containing intronless DNA or mostly coding sequence. Examples of viruses include double-stranded DNA viruses, single-stranded DNA viruses, double-stranded RNA viruses and single-stranded RNA viruses. Examples of double-stranded DNA viruses include, but are not limited to, Epstein-Barr virus (EBV), cytomegalovirus (CMV), herpes simplex virus-1 (HSV-1), HSV-2, varicella-zoster virus (VZV), human herpes virus-6 (HHV-6), HHV-7, HHV-8, poxvirus and adenovirus. Examples of single-stranded DNA viruses include, but are not limited to, parvovirus. Examples of double-stranded RNA viruses include, but are not limited to, retroviruses and reoviruses. Examples of single-stranded RNA viruses include, but are not limited to, paramyxoviruses, myxoviruses, and flaviviruses.

Because the method does not require knowledge of the organism's nucleic acid sequence, it provides a strategy for combating infectious organisms that display a great deal of biological variability (e.g., HIV and HCV). For viruses exhibiting high variability, it is advantageous to use a source of viral nucleic acid material derived from a particular patient, a particular site (e.g., blood, skin, cervix) or representative viral strain circulating in a particular geographical region or patient population, which may differ from prototypical strains of known nucleic acid sequence.

The invention also provides a diagnostic assay. The diagnostic assay can be used to identify the immunological responsiveness of a patient suspected of having a herpetic infection and to predict responsiveness of a subject to a particular course of therapy. The assay comprises exposing T cells of a subject to an antigen of the invention, in the context of an appropriate APC, and testing for immunoreactivity by, for example, measuring IFNγ, proliferation or cytotoxicity. Suitable assays are described in more detail in the Examples.

EXAMPLES

The following examples are presented to illustrate the present invention and to assist one of ordinary skill in making and using the same. The examples are not intended in any way to otherwise limit the scope of the invention.

Example 1

Identification of Viral Epitopes in HSV-2 Tegument Proteins

This example shows the use of expression cloning with full-length viral DNA to identify T-cell antigens. Described herein are five HSV epitopes recognized by lesion-infiltrating T-cells discovered by expression cloning. Also described are several epitopes in VP16 discovered by methods other than expression cloning.

Viruses and Cells

HSV-1 strain E115 (S. L. Spruance and F. S. Chow, 1980, J. Infect. Dis., 142:671–675.), HSV-2 strain 333 (S. Kit et al., 1983, Biochim. Biophys. Acta., 741:158–170), and intertypic recombinant viruses RS1G31 (M. F. Para et al., 1983, J. Virol., 45:1223–1227), DX32 (V. G. Preston et al., 1978, J. Virol. 28:499–517), and RP-2 (D. M. Koelle et al., 1994, J. Virol., 68:2803–2810) were grown and titered in Vero cells (D. M. Koelle et al., 1993, J. Clin. Invest., 91:961–968). Epstein-Barr virus transformed lymphocyte continuous lines (EBV-LCL) (D. M. Koelle et al., 1993, supra) included autologous lines from donors with genital herpes, AMAI, homozygous for HLA DPB1*0402, HOM2, homozygous for HLA DQB10501, MAT, homozygous for HLA DQB1*0201, and ARENT, homozygous for HLA DPB1l2001 (J. G. Bodmer et al., 1996, Tissue Antigens 49:297–321).

HSV-specific T-cells were obtained after approval by the Institutional Review Board. Most clones were derived without secondary in vitro stimulation with antigen. Donors 1, 2, and 4 are numbered as previously described (D. M. Koelle et al., 1994, J. Virol., 68:2803–2810) and were the sources of lesion-derived clones 1.L3D5.10.8, 2.3 and 4.2E1, respectively; clones 2.3 and 4.2E1 have been previously described (D. M. Koelle et al., 1994, supra). Additional lesion-derived clones came from donor ES, from whom clones ESL2.20, ESL3.335, ESL4.34, and ESL4.9 were derived from the second, third, and fourth lesions samples (each separated by one year), and donors RH and KM. Clones 2.3, 4.2E1, ESL2.20, RH.13, and KM.17 were derived directly from herpetic vesicle fluid (D. M. Koelle et al., 1994, J. Infect. Dis. 169:956–961). To derive CD4 TCC ESL4.9, biopsy of a recurrent genital HSV-2 lesion (day 3 of symptoms) was performed and bulk lesion-infiltrating cells expanded with PHA and IL-2 (Schiaperelli Biosystems, Columbia, Md.) in the presence of acyclovir as described (D. M. Koelle et al., 1998, J. Clin. Invest., 101:1500–09). After 16 days, cells were cloned at 1 cell/well (D. M. Koelle et al., 1994, J. Infect. Dis., 169:956–961). Previously described VP16-specific clones 1A.B.25, ESL3.334, and ESL4.34 D. G. Doherty et al., 1996, Human Immunol., 47:149; K. R. Jerome et al., 1998, J. Virol., 72:436–441; D. M. Koelle et al., 1997, Human. Immunol., 53:195–205) were similarly derived from bulk cultures.

Some clones were derived using secondary in vitro stimulation with antigen. To derive additional TCC from donor 1 (D. M. Koelle et al., 1994, J. Virol., 68:2803–2810), PHS-driven bulk cultures were prepared from each of four 2 mm biopsies (day 5 of symptoms) obtained 6 years after the recurrence from which clone 1A.B.25 (above) was derived. After 16 days, 1.5×10$^6$ bulk lymphocytes from one biopsy culture were stimulated with 10 μg/ml HSV-2 VP22 105–190 (see below) and an equal number of autologous irradiated (3300 rad) PBMC in 2 ml T-cell media (D. M. Koelle et al., 1994, J. Infect. Dis., 169:956–961). IL-2 (32 U/ml) was added starting on day 6. TCC 1.L3D5.10.8 was isolated from this line on day 12 as described (D. M. Koelle et al., 1994, supra). To create PBMC-derived TCCSB.17 and BM.17, 1.5×10$^6$ PBMC of HSV-2 seropositive donors SB and BM were stimulated for 12 days with 4 μg/ml baculovirus-derived full length VP16 in 25 well plates; responding cells were cloned at 1 cell/well. TCC and lines were used 10–14 days after last stimulation.

All cell lines were negative for mycoplasma except ARENT. ARENT was initially positive for mycoplasma by DNA probe test (Genprobe, San Diego, Calif.) and was treated with ciprofloxacin at 10 μg/ml (S. M. Gignac et al., 1991, Leukemia 5:162–165) for two weeks prior to utilization with conversion of the test to negative.

Flow Cytometry

A combination of murine mAb to human CD4 (clone SFCI 12T4D11) and CD8 (clone SFC 21Thy2D3 recognizing the α chain of human CD8) (Coulter, Hialeah, Fla.) was used for flow cytometry.

Immunoblot

Lysates of HSV-infected Vero cells were prepared, electrophoresed through 10% SDS-PAGE gels, and transferred to nitrocellulose membrane as described (R. A. Ashley et al., 1988, J. Clin. Microbiol. 26:662–667). Blots were blocked with PBS-0.05% Tween 20-1% nonfat dried milk. Antigen was detected by sequential incubation with 1:100 dilution of mAb P43 specific for the U$_L$49 gene product VP22 (G. D. Elliott et al., 1992, J. Gen. Virol., 73:723–736), affinity purified goat anti-mouse IgM-peroxidase conjugate (Sigma, St. Louis, Mo.), and TMB substrate system (Kirkegaard and Perry, Gaithersberg, Md.) with washes (three×five minutes) in PBS-Tween between each step.

Viral DNA Libraries and Cloning

For subgenomic DNA, the HSV-2 strain HG-52 BamH I w fragment was subcloned from the Bgl II i fragment and gel-purified. Viral DNA was digested with Sma I, BamH I ends were blunted with Klenow DNA polymerase, and DNA fragments were purified by phenol extraction and alcohol precipitation. For whole viral DNA, confluent Vero cells were infected with HSV-2 strain HG52. Total nucleic acids from three 150 cm$^2$ cell cultures were prepared by proteinase K digestion, chloroform-phenol extraction, and isopropanol precipitation. Resultant material was treated with Range H and re-extracted and precipitated. Aliquots (1 μg) of HG52 DNA were digested with Sma I or Alu I and 80% of these digests were combined and recovered as above for creation of expression libraries.

Expression cloning was performed using pUEX vectors (G. M. Bressan et al., 1987, Nucleic Acids Res., 15:10056). pUEX-1, -2, and -3 DNA was linearized with Sma I, dephosphorylated with calf intestinal phosphatase, and gel purified. Approximately 100 ng of vector and 500 ng of DNA fragments were ligated and 10% of ethanol-precipitated reaction mixtures used to transform E. coli strain DH10 Electromas (GIBCO) by electroporation (BTX, San Diego, Calif.) in 1 mm cuvettes. After one hour recovery in 1 ml SOC media, portions were frozen as glycerol stocks (100 μl each), tittered on ampicillin plates at 30° C. (250 μl), or used directly (250 μl) for protein induction to create fusion protein libraries. Several thousand ampicillin-resistant colonies were isolated per transformation. To amplify genomic libraries, glycerol stocks were grown overnight at 30° C. I n2YT-ampicillin and re-frozen.

Confirmatory subcloning of VP22 105–190, $U_L50$ 118–312, and $U_L50$ 118–250 was performed by isolating the 262 base-pair Sma I-Stu I fragment of $U_L49$, the 583 by Sma I fragment of $U_L50$, or the 397 by Sma I-Stu I fragment of $U_L50$, respectively. Fragments were cloned into the appropriate linearized, gel purified pUEX vector and protein expressed in E. coli DH5I. Constructs were confirmed by sequencing.

Antigens

Whole virus preparations containing $10^8$–$10^9$ pfu/ml were UV-inactivated for 30 minutes (A. Mikloska and A. L. Cunningham, 1998, J. Gen. Virol., 79:353–361) and used at a 1:100 final dilution. Peptides of VP22 were synthesized as described (D. M. Koelle et al., 1997, Human. Immunol., 53:195–205) and used as stocks at 2 mg/ml in DMSO. Peptides of $U_L48$, 13 amino acids long and overlapping by four amino acids, VP16 of HSV-2 amino acids 1–416, and full-length VP16, both expressed in baculovirus, were obtained from Chiron Corporation, Emeryville, Calif.

Bacterial-derived protein antigen expression was induced for two hours at 42° C. in cells growing logarithmically ($OD_{600}$ 0.4–0.6) in 2YT-ampicillin broth at 30° C. Protein was purified as described (P. I. Neophytou et al., 1996, Proc. Natl. Acad. Sci. USA, 93:2014–2018), omitting gel purification. Bacterial cultures of 50 ml (libraries) or 5–10 ml cultures (pools and clones) yielded fine particulate suspensions in 200–400 μl PBS (Ca, Mg-free). Protein concentrations were determined by BCA (Pierce, Rockford, Ill.) after solubilizing proteins in 1% SDS at 60° C. for 10 minutes. In some experiments, heat-induced bacteria were washed with PBS and PBS/10 mM EDTA, heated to 56° C. for 10 minutes, and washed in PBS prior to use as antigen.

After identification of an active library of viral DNA, antigen identification used 30–60 clones for subgenomic viral DNA fragments or 2,000–3,000 clones for full-length viral DNA. For the less complex library, 1 ml cultures of each clone were processed as pools of six to eight clones. Individual clones within the active pool, and confirmatory subclones containing known viral DNA fragments, were processed as 5 ml cultures. A combinatorial method (P. I. Neophytou et al., 1996, Proc. Natl. Acad. Sci. USA, 93:2014–2018) was used to screen libraries from whole viral DNA. Glycerol stocks of amplified libraries of transformed bacteria were tittered on ampicillin plates; 20–30 colonies/well were cultured overnight at 30° C. in a 96-well plate in a rotating shaker. Cultures were diluted 1:100 into 1 ml cultures and fusion protein synthesis induced as described above. Portions (400 μl) of cultures were pooled row- and column-wise for protein purification and evaluation in lymphoproliferation assays. If more than one row and column were positive, wells at the intersections of positive rows and one positive column were used to prepare protein from 5–10 ml cultures to definitively identify a positive well. Cultures (n=96 colonies) of bacteria were derived from ampicillin plates seeded with diluted broth from positive wells. These were evaluated as pools (of 12 bacterial colonies) and then individual clones.

Lymphocyte Functional Assays

Triplicate proliferation assay wells contained $10^4$ cloned T-cells, $10^5$ irradiated (3300 rad) PBMC or $2.5\times10^4$ irradiated (8000 rad) EBV-LCL as antigen presenting cells (APC), and antigen in 200 μl T-cell media (D. M. Koelle et al., 1997, Human. Immunol., 53:195–205) in 96-well U-bottom plates. When heat-killed bacteria were used as antigen, the equivalent of $10^5$ cfu/well (prior to inactivation) was added and gentamicin (20 μg/ml) was included. After 72 hours, 1 μCi/well $^3$H thymidine was added for 18 hours, cells were harvested, and incorporation of thymidine evaluated by liquid scintillation counting. Standard deviations were less than 10% of the mean values. Results are reported as mean cpm or as delta cpm=mean cpm for experimental antigen minus mean cpm for control antigen. Control antigen was mock-infected cell lysate for whole viral antigens and pUEX2-derived β-galactosidase for recombinant protein preparations. To determine the reactivity of bulk-cultured lesion-derived T-cells, fusion proteins or control β-galactosidase were used at 10 μg/ml. Glycoproteins B and D and VP16 of HSV-2 were used at 1 μg/ml and assays performed as previously described (D. M. Koelle et al., 1998, J. Clin. Invest., 101:1500–09). To determine HLA restricting loci, HLA DR-specific mAb L243 (V. G. Preston et al., 1978, J. Virol., 28:499–517), HLA DP-specific mAb B7.21 (A. J. Watson et al., 1983, Nature, 304:358–360), or HLA DQ-specific mAb SpV-L3 (H. Spits et al., 1984, Eur. J. Immunol., 14:299–304) were used as described (D. M. Koelle et al., 1994, J. Virol. 68:2803–2810).

Cytolysis assays were performed in triplicate using 4-hour $^{51}$Cr release as described (D. M. Koelle et al., 1993, J. Clin. Invest., 91:961–968). Target EBV-LCL were infected for 18 hours with HSV-3 at a multiplicity of infection of 30 or pulsed with 1.0 μM peptide for 90 minutes prior to washing as described (W. W. Kwok et al., 1996, J. Exp. Med., 183:1253–1258). The effector to target ratio was 20:1. Spontaneous release was less than 28%.

DNA Sequencing

Viral inserts in plasmids in bacteria yielding active proteins were completely sequenced (Taq DyeDeoxy FS kit, Perkin-Elmer ABI, Foster City, Calif.) in both directions starting with primers CATGGCTGAATATCGACGGT (SEQ ID NO: 1; 5' end of insert) and CTAGAGCCGGATC-GATCCGGTC (SEQ ID NO: 2; 3' end of insert) and then internal primers designed as required.

HLA Typing

HLA DR and DQ typing was performed at class II alleles by serologic methods or at the DNA level by reverse dot blot hybridization (E. Mickelson et al., 1993, Tissue Antigens, 41:86–93). HLA DP typing was performed by sequencing (HLA DP kit, Perkin Elmer ABI).

Results

Fine Localization of T-cell Epitopes

Figure 1B:
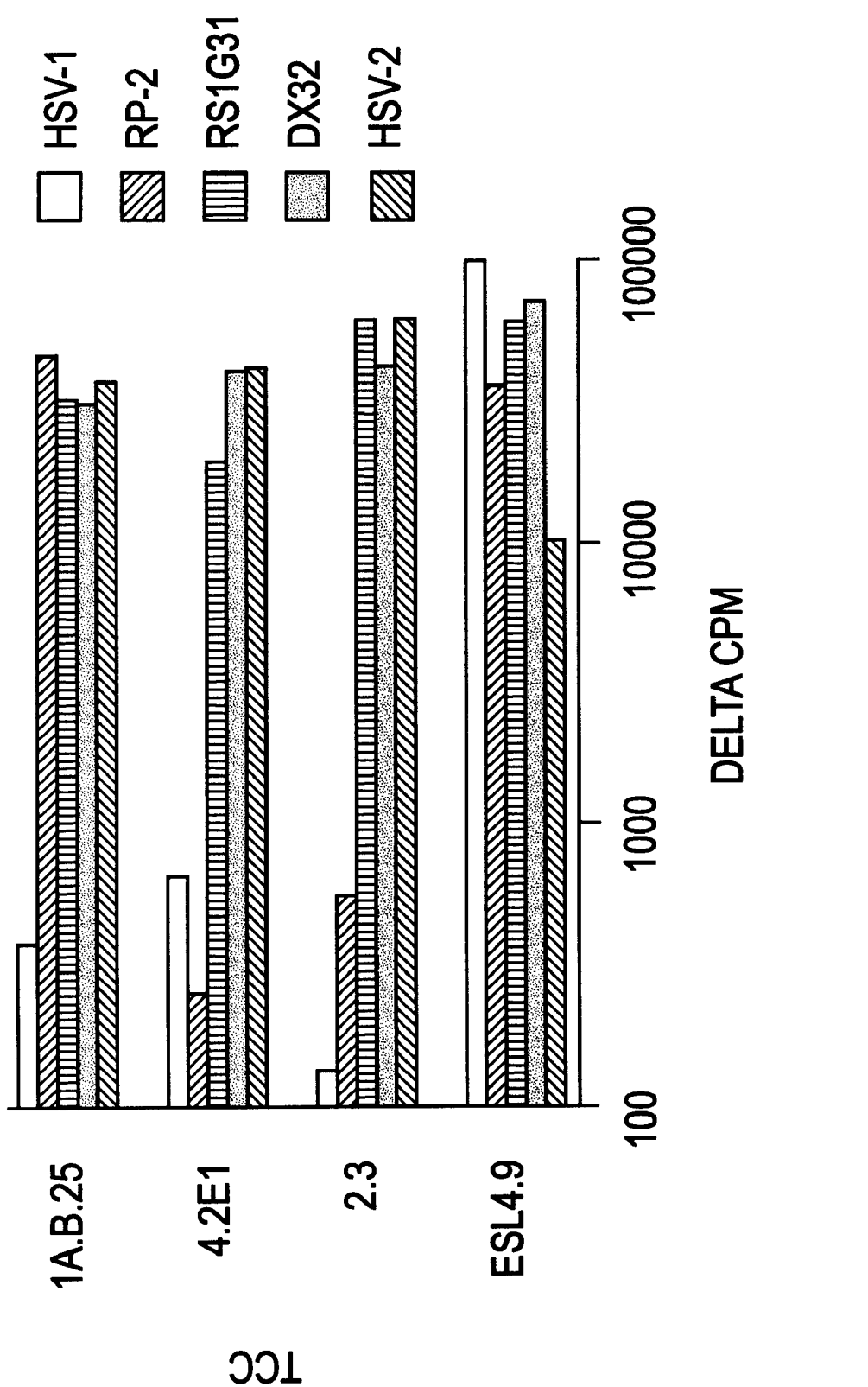
FIG. 1B is a bar graph showing proliferative responses of T-cell clones (TCC) to the indicated IRV. Data are delta CPM [$^3$H] thymidine incorporation compared to media alone, which was less than 500 cpm in each case.
Figure 2:
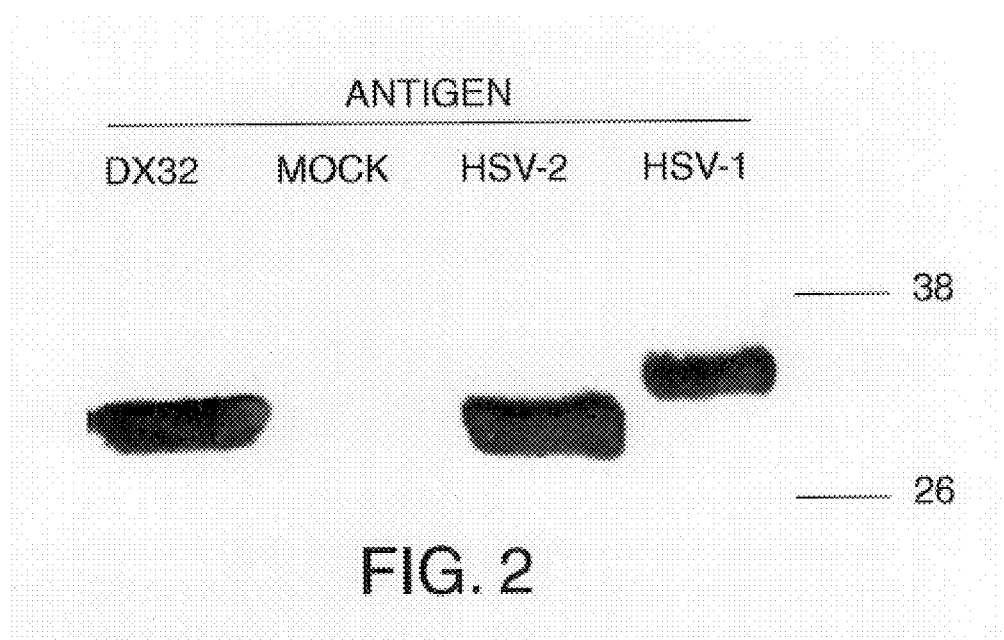
FIG. 2 is an immunoblot showing determination of the HSV viral phenotype of the $U_L49$ gene product (VP22) of IRV DX32. Lysates of mock-infected cells and cells infected with the viral strains DX32, HSV-1 or HSV-2 were separated by SDS-PAGE, blotted, and probed with VP22-specific mAb. The molecular weights kD) of marker proteins are shown at right.

To reduce the complexity of libraries for expression cloning, TCC recognizing antigen(s) partially mapped using HSV-1×HSV-2 intertypic recombinant viruses (IRV) were selected. HSV DNA near 0.7 map unites encodes T-cell antigens in addition to VP16. Epitope mapping for TCC 4.2EI and 2.3 (D. M. Koelle et al., 1994, J. Virol., 68:2803–2810) was improved with IRV DX32 (FIG. 1A). This HSV-2 based virus contains a block of HSV-1 DNA near 0.7 map units (V. G. Preston et al., 1978, J. Virol., 28:499–517). The $U_L48$ gene product has the HSV-2 phenotype, as shown by reactivity with HSV-2 type-specific, VP16-specific (D. M. Koelle et al., 1994, J. Virol., 68:2803–2810) T-cell clone 1A.B.25. The $U_L49$ (FIG. 2) and $U_L50$ gene products (M. V. Williams, 1987, Virology, 156:282–292; F. Wohlrab, 1982, J. Virol., 43:935–942) also have a HSV-2 phenotype. The HSV-2 DNA present in IRV DX32 therefore includes $U_L48$, $U_L49$, $U_L50$, and most likely the intervening $U_L49.5$. Since TCC 4.2E1 and 2.3 react with RS1G31 and DX32, but not with RP2 (FIG. 1B), recognition of $U_L49$, $U_L49.5$, or $U_L50$ is most likely.

Expression Cloning to Determine T-cell Antigens

The BamH I w fragment of HSV-2 was selected for expression cloning, since it contains the $U_L49$, $U_L49.5$, and most of the $U_L50$ coding sequences (A. Cress and S. J. Triezenberg, 1991, Gene, 103:235–238; G. D. Elliott and D. M. Meredith, 1992, J. Gen. Virol., 73:723–736; N. J. Maitland et al., 1982, Infect. Immun., 38:834–842). 70–90% of random colonies contained an insert; all were of viral origin. The most active libraries (Table 1) for each TCC (pUEX1 for TCC 4.2E1, pUEX 3 for TCC 2.3) were selected and an individual reactive bacterial clone detected by sequential testing of pools and individual colonies (Table 2). Clone 1.1.3 encodes a fusion protein eliciting proliferation by TCC 4.2E1. This clone contains a backwards 80 bp Sma I fragment of $U_L49$, a 262 bp Sma I fragment of HSV-2 $U_L49$ DNA predicted to encode amino acids 105 to 190, forward and in-frame with regards to β-galactosidase, and a 246 bp Sma I fragment of $U_L49$ forward but out of frame due to a deletion of a single C residue at the 262 bp Sma I fragment-242 bp Sma I fragment junction. Clone 3.19 contained a 583 bp Sma I fragment encoding amino acids 118–312 of $U_L50$, followed by backwards 80 and 96 bp Sma I fragments of $U_L49$.

with an insert; 80–100% of inserts were of viral origin. For both TCC ESL4.9 and ESL2.20, only the pUEX3 protein library elicited lymphoproliferation (Table 1). Since the libraries were more complex than for those made from the BamH I w fragment, 2,000–3,000 bacterial transformants were screened by a combinatorial method. In preliminary experiments, heat-killed, washed bacteria were found to substitute for inclusion body preparations of protein in lymphoproliferation assays at the pool (5–12 bacterial clones) and final assay stages.

Sequencing of plasmids in positive bacteria showed that TCC ESL4.9 recognized a 44 amino acid fragment of $U_L49$

|  | library[1] | | | control stimuli[2] | |
| --- | --- | --- | --- | --- | --- |
|  | pUEX1-BamH I | pUEX2-BamH I | pUEX3-BamH I | | |
| TCC | "w"-Sma I | "w"-Sma I | "w"-Sma I | media | HSV-2 |
| 4.2E1 | 10,105 | 4,150 | 1,903 | 286 | 21,591 |
| 2.3 | 418 | 785 | 2,279 | 102 | 11,014 |
|  | library[1] | | | control stimuli[2] | |
|  | pUEX1-HG52- | pUEX2-HG52- | pUEX3-HG52- | | |
| TCC | Sma I-Alu I | Sma I-Alu I | Sma I-Alu I | media | HSV-2 |
| ESL4.9 | −52 | −25 | 16,235 | 146 | 66,013 |
| ESL2.20 | 1 | 768 | 5,427 | 123 | 13,359 |

[1]Library names list expression vector, name of HSV-2 restriction fragment or strain of full-length viral DNA, and restriction enzyme(s) used to digest viral DNA.
[2]$10^5$ autologous irradiated (3300 rad) PBMC and either mock-infected cell lysate or UV-treated HSV-2 antigen.

Figure 3A:
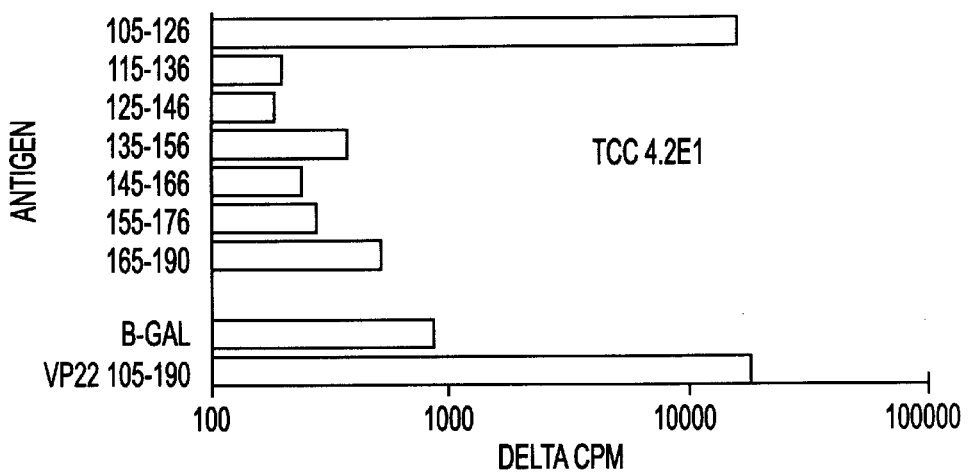
FIG. 3A is a bar graph showing T-cell proliferation elicited by various peptide epitopes in VP22 of HSV-2 using TCC 4.2E1. Antigen-presenting cells (APC) were autologous EBV-LCL. Antigens included β-galactosidase and fusion proteins used at 10 μg/ml and peptides used at 3 μM. Data are delta cpm [$^3$H] thymidine incorporation compared to media alone, which was less than 500 cpm in each case.
Figure 3B:
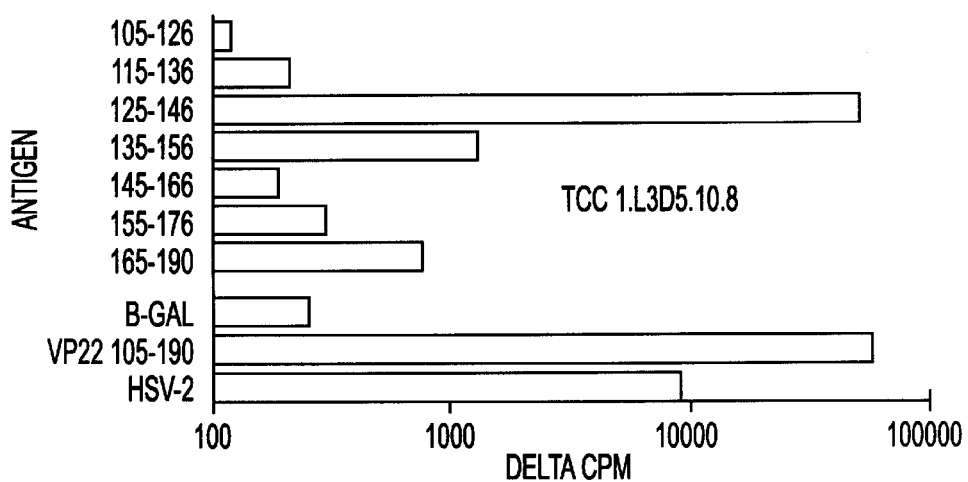
FIG. 3B is a bar graph showing T-cell proliferation elicited by various peptide epitopes in VP22 of HSV-2 using TCC 1.L3D5.10.8. APC were autologous PBMC. Antigens included β-galactosidase and fusion proteins used at 10 μg/ml and peptides used at 1 μM. Data are delta cpm [$^3$H] thymidine incorporation compared to media alone, which was less than 500 cpm in each case.
Figure 3C:
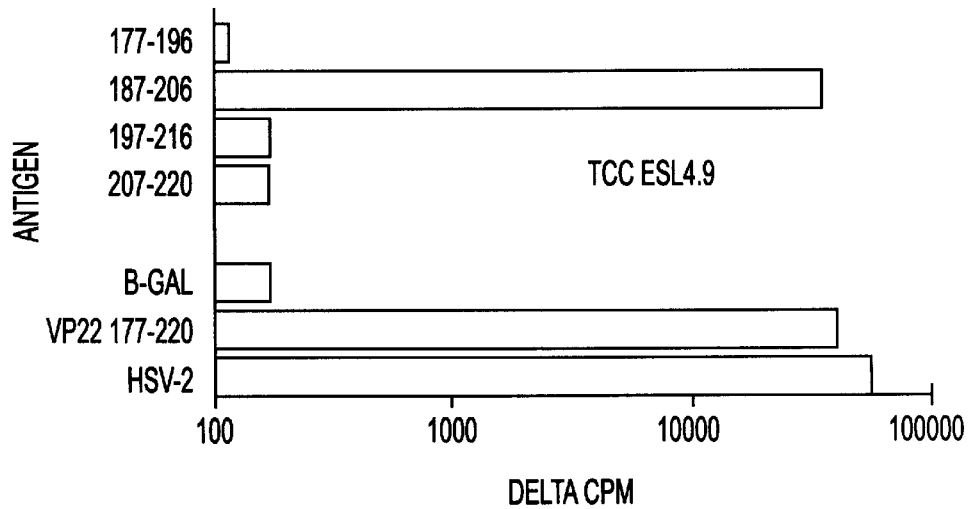
FIG. 3C is a bar graph showing T-cell proliferation elicited by various peptide epitopes in VP22 of HSV-2 using TCC ESL4.9. APC were autologous PBMC. Antigens included β-galactosidase and fusion proteins used at 10 μg/ml and peptides used at 1 μM. Data are delta cpm [$^3$H] thymidine incorporation compared to media alone, which was less than 500 cpm in each case.

Identification of T-cell antigens was confirmed by targeted subcloning and overlapping peptides. The 262 bp Sma I fragment of $U_L49$ of HSV-2 encoding amino acids 105–190 was subcloned into pUEX3 to yield plasmid 49.262.12. This protein stimulated TCC 4.2E1 (Table 2). Only peptide 105–126 of VP22 of HSV-2 (GGPVGAGGRSHAPPARTPKMTR; SEQ ID NO: 3) was stimulatory FIG. 3). DNA fragments encoding $U_L50$ 118–312 and 118–250 were subcloned into pUEX3. Fusion proteins expressing these fragments were active (Table 2).

gene product VP22 (amino acids 177–220), while TCC ESL2.20 recognized a 34 amino acid fragment of $U_L21$ (amino acids 148–181) (Table 2). In both cases single Alu I fragments of HSV-2 DNA were inserted in-frame and forwards. Peptide mapping revealed that amino acids 187–206 (FIG. 3C) stimulated TCC ESL4.9.

Fusion Proteins as Probes of Bulk Lesion-infiltrating T-cells

Newly discovered T-cell antigens were added to the panel of HSV antigens used to probe bulk cultures of lesion-infiltrating T-cells. The first available specimens were a set of four biopsies (2 mm each) obtained from day 5 (virus

TABLE 2

Antigenic specificity of HSV-2 reactive TCC. Bacterially-derived recombinant fusion protein antigens were used at 1:900 dilution. Autologous EBV-LCL (clone 4.2E1) or PBMC were used as APC. Data are delta cpm [$^3$H] thymidine incorporation compared to media, which was less than 500 cpm in each case.

|  | recombinant antigen | | | control antigens | | |
| --- | --- | --- | --- | --- | --- | --- |
| TCC | Clone name | viral sequence[1] | cpm | pUEX2 β-gal | HSV-1 | HSV-2 |
| 4.2E1 | 1.1.3 | VP22 105–190 | 4,875 | 93 | nd | nd |
|  | 49.262.12[2] | VP22 105–190 | 6,898 | | | |
| 2.3 | 3.19 | $U_L50$ 118–312 | 43,971 | 231 | 543 | 53,032 |
|  | 50.583.44[3] | $U_L50$ 118–312 | 34,453 | | | |
|  | 50.397[3] | $U_L50$ 118–250 | 66,501 | | | |
| ESL4.9 | C11 | VP22 177–220 | 59,400 | 166 | 112,803 | 64,685 |
| ESL2.20 | C9D10 | $U_L21$ 148–181 | 23,543 | 173 | 0 | 37,989 |

[1]Amino acids predicted forward and in-frame with β-galactosidase from sequence data.
[2]Confirmatory subclone of 1.1.3 containing only a 262 bp Sma I fragment of $U_L49$ DNA forward and in-frame with pUEX3.
[3]Confirmatory subclones of 3.19 containing a 583 bp Sma I fragment of ULSO or a 397 bp Sma I-Stu I fragment of $U_L50$ DNA forward and in-frame with pUEX3.

Evaluation of random colonies from full-length HSV-2 DNA libraries showed that 80–100% contained plasmids culture positive) of a buttock recurrence of HSV-2 from patient 1 (D. M. Koelle et al., 1998, J. Clin. Invest.

101:1500–09; D. M. Koelle et al., 1994, J. Virol., 68:2803–2810). All four biopsies showed reactivity with VP22 105–190 but not β-galactosidase, glycoproteins B or D, or VP16. TCC were derived after restimulating the original bulk culture for one cycle with VP22 105–190 fusion protein. Proliferative responses of TCC 1.L3D5.10.8 (FIG. 3B) to VP22 (105–190) and constituent peptides document a third T-cell epitope in VP22 contained within amino acids 125–146.

Definition of Additional T-cell Epitopes in Tegument protein VP16

Three epitopes within VP16 (Table 3), all HSV-2 type-specific were previously identified (K. R. Jerome et al., 1998, J. Virol., 72:436–441), and proliferative responses to full-length VP16 in bulk cultures of genital HSV-2 lesion-infiltrating lymphocytes from four of seven (57%) patients were detected (D. M. Koelle et al., 1998, J. Clin. Invest., 101:1500–09). Additional peptide epitopes were sought within VP16 by two strategies. The first strategy involved screening panels of clones recovered from lesion vesicle fluid for reactivity with recombinant VP16 of HSV-2 followed by epitope mapping with peptides. Peptides containing amino acids 185–197 and the overlapping pair 209–221 and 213–225 were stimulatory for TCC RH.13 and KM.7, respectively (Table 3). All other VP16 peptides were negative (<500 cpm). The second strategy involved using PBMC as starting material and secondary in vitro stimulation with recombinant baculovirus-derived VP16. Clones BM.17 and SB.17) from two individuals recognized the same peptide (amino acids 437–449) as well as β-gal-VP16 fusion protein and whole virus. All three newly defined VP16 epitopes were type-common, shared by HSV-1 and HSV-2 whole virus preparations, as expected from sequence data (A. Cress and S. J. Triezenberg, 1991, Gene, 103:235–238).

HLA Restriction

The HLA restriction of the TCC recognizing antigens encoded near 0.7 map units was determined in detail. Proliferation of TCC 4.2E1, specific for VP22 105–126, is inhibited 84% by anti-DP, but less than 20% by anti-DR or anti-DQ mAb. TCC 4.2E1 is from a DPB1*2001/DPB1*0402 heterozygous donor. Allogeneic EBV-LCL bearing DPB1*2001, but not DPB1*0402, present antigen (Table 4), establishing restriction by DPB1*2001. Proliferation of TCC 2.3, specific for $U_L50$, was inhibited by anti-DR but not anti-DP or anti-DQ mAb. This clone is from a DRB1*0301/BRB1*0701 heterozygous donor. Allogeneic PBMC from a DRB1*0301 donor presented antigen, consistent with binding of antigenic peptide to this allele. However, presentation by the linked DR gene products DRw52 or DRw53, cannot be ruled out. Additional HLA restriction studies are summarized in Table 5.

TABLE 4

Determination of restricting HLA allele of lesion-derived CD4 TCC 4.2E1 and 2.3. Antigens were β-gal fusion proteins (Table 2) at 1:900 dilution. Data are delta cpm [$^3$H] thymidine incorporation compared to media, which was less than 500 cpm in each case.

| T-cell clone | antigen | APC | HLA type[1] | delta cpm[2] |
|---|---|---|---|---|
| 4.2E1 | 1.1.3 | autologous EBV-LCL | DPB1*0402, 2001 | 30,719 |
| | | AMAI EBV-LCL | DPB1*0402 | 2,732 |
| | | ARENT EBV-LCL | DPB1*2001 | 26,218 |

TABLE 3

Epitopes within VP16 of HSV-2 recognized by lesion- and PBMC-derived CD4 TCC. Data are delta cpm [$^3$H] thymidine incorporation compared to media, which was less than 500 cpm in each case.

| TCC | | whole virus antigen | | recombinant HSV-2 protein[1] | | HSV-2 VP16 peptide | |
|---|---|---|---|---|---|---|---|
| name | origin | HSV-1 | HSV-2 | VP16 1-492 | β-gal-BP16 180-492 | amino acids | delta cpm |
| newly reported epitopes | | | | | | | |
| RH.13 | lesion | 3,340 | 3,407 | 32,991 | nd | 185–197 | 55,614 |
| KM.7 | lesion | 6,093 | 5,847 | 5,627 | nd | 209–221 | 10,075 |
| BM.17 | PBMC | 30,784 | 13,777 | nd | 45,958 | 437–449 | 79,723 |
| SB.17 | PBMC | 2,207 | 4,187 | nd | 12,178 | 437–449 | 36,442 |
| previously reported epitopes | | | | | | | |
| ESL4.34 | lesion | 256 | 8,780 | 17,302 | nd | 389–401 | 12,968 |
| | | | | | | 393–405 | 95,942 |
| ESL3.334 | lesion | 253 | 14,232 | 22,754 | 16,434 | 430–444 | 27,283 |
| 1A.B.25 | lesion | 414 | 33.493 | 24,919 | 41,123 | 431–440 | 38,664 |

[1]VP16 1-492 (baculovirus-derived) was used at 1 μg/ml. β-gal-BP16 180-492 was used at 1:1,000 dilution.
[2]Peptides were used at 1 μM.
na = not available
nd = not done TABLE 4-continued Determination of restricting HLA allele of lesion-derived CD4 TCC 4.2E1 and 2.3. Antigens were β-gal fusion proteins (Table 2) at 1:900 dilution. Data are delta cpm [$^3$H] thymidine incorporation compared to media, which was less than 500 cpm in each case.

| T-cell clone | antigen | APC | HLA type[1] | delta cpm[2] |
|---|---|---|---|---|
| 2.3 | 50.583.44 | autologous PBMC | DRB1*0301, 0701 | 8,964 |
|  |  | allogeneic PBMC A | DRB1*0701, 1001 | 45 |
|  |  | allogeneic PBMC B | DRB1*0301, 1301 | 19,223 |

[1]HLA type at the HLA class II locus as determined by inhibition with mAb.
[2]In comparison to pUEX2 control protein (1:1000 dilution) with the same APC, which caused less than 500 cpm [$^3$H] thymidine incorporation in each case.

TABLE 5

Cytolytic activity of lesion-derived, tegument-specific CD4 TCC with summary of fine specificity and HLA restriction. Results are percent specific release at an effector to target ratio of 20:1 except ESL4.34 (10:1). Auto = autologous EBV-LCL as target cells; allo = allogeneic EBV-LCL mismatched at the relevant HLA locus (if known) or mismatch at HLA DR and DQ.

| | | | cytolysis assay target | | | | | |
|---|---|---|---|---|---|---|---|---|
| TCC | specificity[1] | HLA restriction[2] | auto HSV-2 | auto peptide | auto mock | allo HSV-2 | allo peptide | allo mock |
| newly reported epitopes | | | | | | | | |
| 4.2E1 | VP22 105–126 | DPB1*2001 | 20.7 | 44.2 | −4.1 | −2.9 | −1.7 | 4.6 |
| ESL4.9 | VP22 187–206 | DR[3] | −0.6 | 20.2 | 1.3 | 0 | 0 | 0 |
| ESL2.20 | $U_L$21 148–181 | DR[3] | 2.7 | na | 0.9 | 0 | na | 0 |
| 1.L3D5.10.8 | VP22 125–146 | DR[4] | 1.1 | 61.1 | −0.3 | −0.4 | −0.6 | −0.4 |
| 1.L3D5.10.12 | VP22 125–146 | DR[4] | 2.5 | 57.6 | 1.6 | −0.1 | −2.5 | −1.4 |
| RH.13 | VP16 185–197 | DR[4] | 62.5 | 55.2 | −0.9 | 9.6 | 0.3 | 1.8 |
| KM.7 | VP16 209–221 | DR[4] | 38.7 | 43.6 | 2.7 | −2.2 | 4.3 | −1.1 |
| BM.17 | VP16 437–449 | DQB1*0501 | 10.1 | 28.5 | −0.3 | nd | nd | nd |
| SB.17 | VP16 437–449 | DQB1*0501 | 48.7 | 60.6 | 5.4 | nd | nd | nd |
| 2.3 | $U_L$50 118–250 | DRB1*0301 | 0.8 | na | 0 | 1.1 | na | 0 |
| previously described epitopes | | | | | | | | |
| ESL4.34 | VP16 393–405 | DRB1*0402 | 2.1 | 10.4 | 1.0 | 0.5 | 0.6 | 0.3 |
| BSL3.334 | VP16 430–444 | DQB1*0302 | 12.3 | 33.6 | 0.7 | 1.4 | 0.3 | 2.2 |
| 1A.B.25 | VP16 431–440 | DQB1*0201 | 24.3 | 42.2 | 1.9 | 1.7 | 2.1 | −0.4 | na = not available since epitope mapping was not done and synthetic antigenic peptide was not made.
nd = not done.

Figure 4:
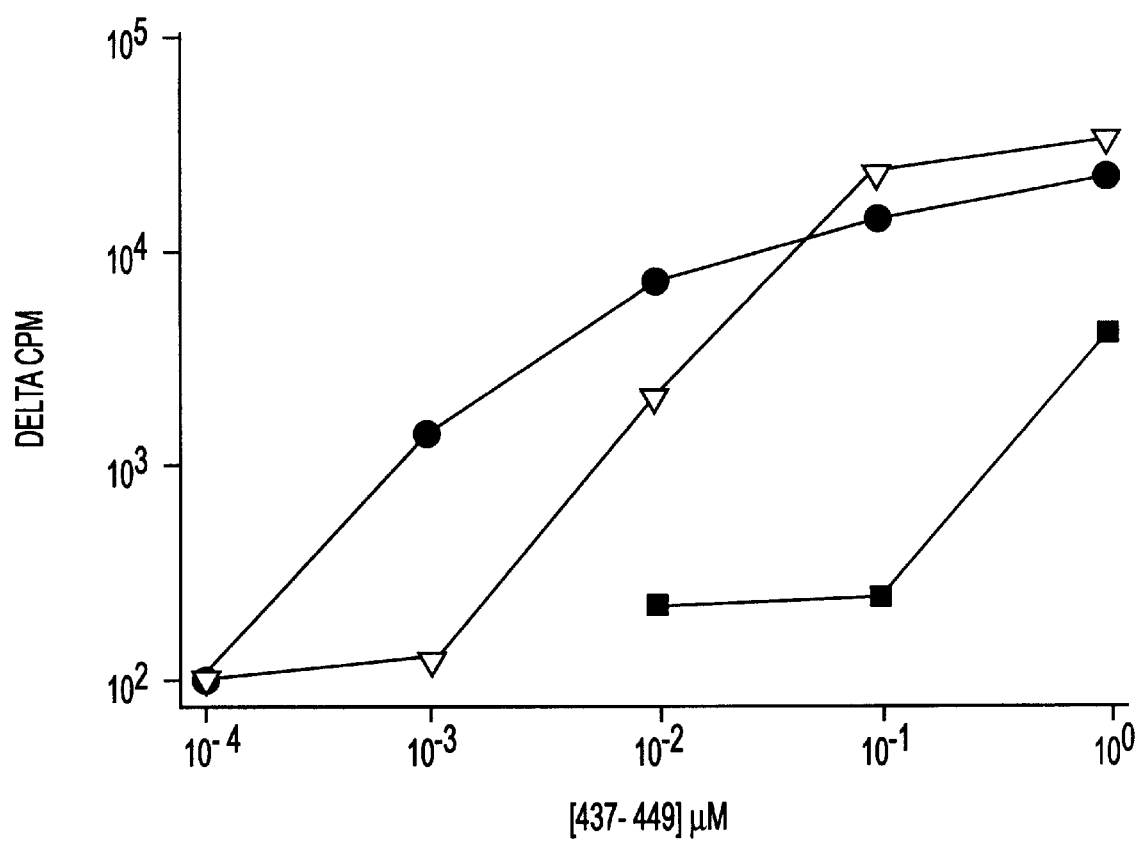
FIG. 4 is a line graph showing HLA restriction element for T-cell clone BM.17 response to peptide 437–449 of VP16 of HSV-2. Proliferative responses are plotted versus concentration of viral peptide. Antigen presenting cells are EBV-LCL that are either autologous (closed circles), homozygous for HLA DQB1*0501 (open triangles), or homozygous for HLA DQB1*0201 (squares).

The HLA restriction of TCC BM.17 was studied in detail. Proliferation of TCC BM.17 and the similar clone SB.17 was inhibited 90% by anti-DQ, but less than 25% by anti-DR or anti-DP mAb. Donors BM and SB are heterozygous for HLA DQB1*0201/0501. At high concentrations of peptide, both DQB1*0201- and DQB1*0501 homozygous EBV-LCL appeared to present antigen to TCC BM.17. However, DQB1*0501 homozygous cells presented peptide much more efficiently than DQB1*0201 homozygous cells (FIG. 4). Thus, three different but overlapping epitopes in VP16 431–449 are presented by HLA DQB1*0302, DQB1*0201, and DQB1*0501.

CTL Activity of Tegument-specific CD4 T-cell Clones

Cytotoxic activities of the CD4 TCC with newly and previously identified specificities were tested using EBV-LCL target cells (Table 5). All clones tested displayed cytolytic activity towards peptide-loaded target cells. Cytolytic activity against target cells infected with HSV-2 showed greater variability. VP22-specific TCC 4.2E 1 was active, while VP22-specific TCC from other donors were not. Among the seven VP16-specific T-cell clones tested, six displayed greater than 10% cytotoxicity towards HSV-2-infected target cells. The single $U_L$21- and $U_L$50-specific TCC were not active against virally-infected target cells.

Discussion

HSV-specific T-cells selectively infiltrate recurrent genital HSV-2 lesions (D. M. Koelle et al., 1994, J. Infect. Dis., 169:956–961). Local CTL activity, with CD4 and CD8-mediated components, is correlated with viral clearance (D. M. Koelle et al., 1998, J. Clin. Invest. 101:1500–09). The antigens recognized by local HSV-specific T cells are diverse and in many cases unknown (D. M. Koelle et al., 1994, J. Virol., 68:2803–2810). This example documents recognition of tegument proteins VP22 and $U_L$21 and the viral dUTPase, and provides new information about tegument protein VP16.

The expression cloning system described herein works well with HSV. Genomic double stranded DNA can be used directly since introns are rare in the HSV genome. The same HSV-2 strain, HG52 (A. Dolan et al., 1998, J. Virol. 72:2010–2021) was used to screen candidate lesion-derived TCC and make protein libraries. The relatively low degree of strain variability (M. J. Novotny et al., 1996, Virology, 221:1–13) between HSV-2 strains in the donors and HG52 might rarely lead to omission of epitope(s) recognized in vivo; application to viruses with more strain variation would benefit from the use of autologous isolates.

Notably, reactivity with VP22 was detected in two independent expression cloning experiments with lesion-infiltrating TCC from two donors. VP22 reactivity was also detected during screening of the first available set of bulk lesion-infiltrating lymphocyte cultures. Ten additional clones from three patients have been negative with the disclosed fragments of $U_L$49, $U_L$21, and $U_L$50.

Tegument antigens may be suitable targets for lesion-infiltrating CD4 T-cells because of their abundance. VP16 and VP22 are present in large amounts: on the order of 1.6×10³ molecules of VP16 (Y. Zhang and J. L. C. McKnight, 1993, J. Virol., 67:1482–1492) and 2.5–2.8×10³ molecules of VP22 (J. Leslie et al., 1996, Virology, 220:60–68) are incorporated into each virion in HSV-1. Less information is available for $U_L21$ (J. D. Baines et al., 1994, J. Virol. 68:2929–2936; J. A. Blaho et al., 1994, J. Biol. Chem. 269:17401–17410). The viral dUTPase is the first non-virion component documented to be a target of the HSV-specific CD4 T-cell response. This enzyme, like VP16 and VP22, localizes to the nucleus of HSV-2 (although not HSV-1) infected cells (F. Wohlrab et al., 1982, J. Virol., 43:935–942). Antigen presentation in vivo may occur after endogenous synthesis of dUTPase in infected cells, or scavenging of dUTPase antigen from infected cell debris. Lysis of HSV-infected cells by dUTPase-specific TCC 4.2E1 indicates that, at least in vitro, presentation of endogenous antigen can occur.

Because polypeptides expressed as C-terminal fusion to VP22 can be co-transported into cells, expression of proteins as VP22 fusions may be of interest as a type of adjuvant preparation. This can be tested by expression of heterologous epitopes in VP22. VP16 and VP22 of HSV-1 are strongly, noncovalently associated in infected cells as shown by coimmunoprecipitation. These proteins co-localize in the perinuclear area of cells (G. Elliott et al., 1995, J. Virol., 69:7932–7941; G. D. Elliott et al., 1992, J. Gen. Virol., 73:723–736). This association may play a role in stimulating the apparent high level of CD4 T-cell response to VP16.

In summary, expression cloning has allowed discovery of novel HSV T-cell antigens. The in situ enrichment of antigen-specific CD4 T-cells in lesions allows study of the antigenic repertoire unbiased by secondary in vitro stimulation with antigen. The favorable characteristics of the HSV genome allow direct use of libraries of whole viral DNA. Tegument proteins are candidates together with membrane glycoproteins for use as HSV vaccines in humans.

Example 2

Identification of Additional HSV-2 Viral Epitopes

The expression cloning method described in Example 1 above was employed to identify additional T cell antigens of HSV-2. The results revealed two additional antigens. One is found at amino acids 1078–1319 of $U_L19$. $U_L19$ is also known as major capsid antigen or as VP5. The other antigen is amino acids 1–273 of US8, also known as glycoprotein E. The US8 antigen was identified using T cells derived from a cervical sample.

Example 3

Efficacy of Full-length $U_L49$ and $U_L50$

This Example shows that the full-length $U_L49$ and $U_L50$ proteins are effective at stimulating T cell proliferation. The data demonstrate the antigenicity of full-length $U_L49$ expressed in E. coli and in Cos-7 cells, and the antigenicity of full-length $U_L50$ expressed in Cos-7 cells. These results confirm that the antigens described hereinabove were accurately identified.

To express full-length $U_L49$ protein of HSV-2 in a prokaryotic system, the gene was cloned by PCR from DNA prepared from HSV type 2 strain HG52 using primers GGAAGATCTACCTCTCGCCGCTCCGTCA (SEQ ID NO: 4) at the 5' end of the gene and CCGGAATTCT-TGTCTGTCGTCTGAACGCG (SEQ ID NO: 5) at the 3' end of the gene. PCR product was digested with Bgl II and EcoR I and cloned into the Bgl II and EcoR I sites in the TA cloning vector pcR2.1-Topo (Invitrogen). The gene was then subcloned into the vector pTrcHisB (Invitrogen) and then into pGEX-2T (Pharmacia). The sequence of the HSV-2 $U_L49$ clone had one coding mutation compared to the published sequence (Dolan 1998): amino acid 244 was mutated from serine to proline. The predicted amino acid sequence of the expressed protein also is missing the initial methionine. $U_L49$ contains an N-terminal fusion domain derived from vector pGEX2T. This plasmid is named pGEX2T-$U_L$49HSV2.

To make prokaryotically expressed full length $U_L49$ of HSV-2, pGEX2TU-L49HSV2 or control empty vector was transformed into E. coli strain BL21 Bacteria in log-phase growth were adjusted to an $OD_{600}$ of 0.4 in LB-ampicillin media. To some tubes isopropyl beta-D-thiogalactopyranoside (IPTG) was added to 0.3 mM. Bacteria were cultured for 1.5 hours at 37° C. with rotation. Bacteria were collected by centrifugation and washed 3× in PBS containing 1 mM EDTA, heated to 65° C. for 10 minutes, and washed twice more with PBS, and resuspended at approximately 1×10⁹ bacteria/ml in T-cell medium. Heat-killed bacterial suspensions were used as test antigen.

To express full-length $U_L49$ protein of HSV-2 in a eukaryotic system, the gene was separately re-amplified by polymerase chain reaction using a high-fidelity DNA polymerase with proof-reading function. The same primers and template were used. The gene was cloned directly into the Bgl II and EcoR I sites of pEGFP-C1 (Clontech). The entire $U_L49$ gene was sequenced and agreed with published sequence. The predicted amino acid sequence of the expressed protein is identical to that predicted for viral $U_L49$ except that the initial methionine at amino acid 1 is missing. A N-terminal fusion domain derived from vector pEGFP-C1 is also predicted to be expressed. This plasmid is named pEGFP-C1-UL49HSV2.

To make eukaryotically expressed full length $U_L49$ of HSV-2, pEGFP-C1-UL49HSV2 plasmid DNA or pEGFP-C1vector control DNA was transfected into Cos-7 cells by lipofection. After 48 hours, cells were scraped and sonicated and a supernatant and pellet phase prepared. Cells from a 9.4 cm² dish were used to prepare 300 microliters of supernatant. The pellet from a 9.4 cm² dish was resuspended in 300 microliters medium. Supernatant and pellet preparations were used as test antigens.

To express full-length UL50 protein of HSV-2 in a eukaryotic system, the gene was cloned by PCR using high-fidelity thermostable DNA polymerase with proof-reading function from DNA prepared from HSV type 2 strain HG52 DNA using primers TAAGGTACCTATGAGT-CAGTGGGGGCCC (SEQ ID NO: 6) at the 5' end of the gene and AAACTGCAGGAGGCGCGGTCTAGATGC (SEQ ID NO: 7) at the 3' end of the gene. The target DNA was used as a clone of the Bgl II i fragment cloned into pUC9. The PCR product was digested with Kpn I and Pst I and cloned into similarly digested pcDNA3.1-myc-his-B (Invitrogen). The sequence was confirmed at the junctions between vector and insert. The plasmid is named pcDNA3.1-myc-his-B-UL50HSV2. The predicted amino acid sequence of the expressed protein is identical to that predicted for viral $U_L50$. A N-terminal fusion domain derived from vector pcDNA3.1-myc-his-B is also predicted to be expressed. To make eukaryotically expressed full-length $U_L50$ of HSV-2 as test antigens, the Cos-7 system was used exactly as described above for $U_L49$. Control antigen for $U_L50$ was made by transfecting Cos-7 cells with pcDNA3.1-myc-his-B.

These test antigens were added to assay wells (96-well, U-bottom) in 200 microliters of T-cell medium containing 1×10⁵ autologous irradiated peripheral blood mononuclear cells (PBMC) per well and 1×10⁴ lesion-derived CD4-bearing T-cell clone ESL4.9 for $U_L49$ or clone 2.3 for $U_L50$ (Koelle et al, 1994 and 1998 and original patent application).

Assays were performed in duplicate or triplicate. After three days, $^3$H thymidine incorporation was measured as described in Example 1.

Results are expressed as stimulation index (mean cpm $^3$H thymidine incorporation test antigen/mean cpm $^3$H thymidine incorporation media control) and delta cpm (mean cpm $^3$H thymidine incorporation test antigen minus mean cpm $^3$H thymidine incorporation media control). Positive and negative control antigens were run as indicated and as described in Example 1.

TABLE 6

Antigenicity of full-length HSV-2 UL49 expressed prokaryotically in *E. coli* BL21

| antigen | final dilution | delta cpm | stimulation index |
|---|---|---|---|
| UV HSV-2 | 1:100 | 26,823 | 386 |
| heat-killed pGEX2 | 1:4 | −11 | 0.84 |
| heat-killed pGEX2 | 1:40 | −25 | 0.64 |
| heat-killed pGEX2 | 1:400 | −8 | 0.89 |
| heat-killed pGEX2-UL49HSV2 | 1:4 | 9,413 | 135 |
| heat-killed pGEX2-UL49HSV2 | 1:40 | 10,526 | 152 |
| heat-killed pGEX2-UL49HSV2 | 1:400 | 5,021 | 73 |

TABLE 7

Antigenicity of full-length HSV-2 UL49 expressed eukaryotically in Cos-7 cells

| antigen | final dilution | delta CPM | stimulation index |
|---|---|---|---|
| UV-mock virus | 1:100 | −4 | 0.96 |
| UV HSV-2 | 1:100 | 46,510 | 470 |
| supernatant of control-transfected cells | 1:4 | 8 | 1.08 |
| pellet of control-transfected cells | 1:4 | 131 | 2.32 |
| supernatant of UL49-transfected cells | 1:4 | 1,512 | 16.3 |
| pellet of UL49-transfected cells | 1:4 | 84,951 | 859 |
| pellet of UL49-transfected cells | 1:40 | 35,753 | 362 |
| pellet of UL49-transfected cells | 1:400 | 29,854 | 302 |

TABLE 8

Antigenicity of full-length HSV-2 UL50 expressed eukaryotically in Cos-7 cells

| antigen | final dilution | delta CPM | stimulation index |
|---|---|---|---|
| UV-mock virus | 1:100 | −43 | 0.89 |
| UV HSV-2 | 1:100 | 52,990 | 135 |
| supernatant of control-transfected cells | 1:5 | 302 | 1.86 |
| pellet of control-transfected cells | 1:5 | 34 | 1.09 |
| supernatant of UL50-transfected cells | 1:5 | 26,910 | 77.7 |
| supernatant of UL50-transfected cells | 1:20 | 33,063 | 95.2 |
| supernatant of UL50-transfected cells | 1:100 | 20,438 | 59.2 |
| supernatant of UL50-transfected cells | 1:500 | 2,346 | 7.7 |
| pellet of UL50-transfected cells | 1:5 | 42,820 | 123.0 |
| pellet of UL50-transfected cells | 1:20 | 18,487 | 53.7 |

TABLE 8-continued

Antigenicity of full-length HSV-2 UL50 expressed eukaryotically in Cos-7 cells

| antigen | final dilution | delta CPM | stimulation index |
|---|---|---|---|
| pellet of UL50-transfected cells | 1:100 | 8,947 | 26.5 |
| pellet of UL50-transfected cells | 1:500 | 864 | 3.5 |

These results show that HSV-2 proteins $U_L49$ and $U_L50$ retain their immunogenicity when expressed as full-length proteins. $U_L49$ was studied in prokaryotic and eukaryotic systems and $U_L50$ in a eukaryotic system.

Example 4

Efficacy of Full-length $U_L21$

To express full-length $U_L21$ protein of HSV-2 in a eukaryotic system, the gene was cloned by PCR using high-fidelity thermostable DNA polymerase with proof-reading function from DNA prepared from HSV type 2 strain HG52 DNA using primers CTGGGATCCATGGAGCTCAGCTATGC-CACC (SEQ ID NO: 8) at the 5' end of the gene and CGCGAATTCTCACACAGACTGGCCGTGCTG (SEQ ID NO: 9) at the 3' end of the gene. The PCR product was digested with BamH I and EcoR I and cloned into similarly digested pGEX-5T. From there, it was cut out with BamH I and Xho I and cloned into similarly digested pcDNA3.1-myc-his-C (Invitrogen). The sequence was confirmed at the junctions between vector and insert. The plasmid is named pcDNA3.1-myc-his-C-UL21HSV2. The predicted amino acid sequence of the expressed protein is identical to that predicted for viral $U_L21$. A N-terminal fusion domain derived from vector pcDNA3.1-myc-his-B is also predicted to be expressed. To make eukaryotically expressed full-length $U_L21$ of HSV-2 as test antigens, the Cos-7 system was used exactly as described for $U_L49$. Control antigen for $U_L21$ was made by transfecting Cos-7 cells with pcDNA3.1-myc-his-B.

The $U_L21$ test antigens were added to assay wells (96-well, U-bottom) in 200 microliters of T-cell medium containing $1 \times 10^5$ autologous irradiated peripheral blood mononuclear cells (PBMC) per well and $1 \times 10^4$ lesion-derived CD4-bearing T-cell clone ESL2.20 (Koelle et al, 1994 and 1998 and Example 1 above). Assays were performed in triplicate. After three days, $^3$H thymidine incorporation was measured as described in Example 1. Results are expressed as stimulation index (mean cpm $^3$H thymidine incorporation test antigen/mean cpm $^3$H thymidine incorporation media control) and delta cpm (mean cpm $^3$H thymidine incorporation test antigen minus mean cpm $^3$H thymidine incorporation media control). Positive and negative control antigens were run as indicated; details of which can be found in Example 1. Results are presented in Table 9.

TABLE 9

Antigenicity of full-length HSV-2 UL21 expressed eukaryotically in Cos-7 cells..

| antigen | final dilution | delta CPM | stimulation index |
|---|---|---|---|
| UV-mock virus | 1:100 | 43 | 1.75 |
| UV HSV-2 | 1:100 | 5620 | 97.9 |
| supernatant of control-transfected cells | 1:20 | −9 | 0.83 |
| pellet of control-transfected | 1:20 | −9 | 0.83 |

TABLE 9-continued

Antigenicity of full-length HSV-2 UL21 expressed eukaryotically in Cos-7 cells..

| antigen | final dilution | delta CPM | stimulation index |
|---|---|---|---|
| cells | | | |
| supernatant of UL21-transfected cells | 1:20 | 1870 | 33.25 |
| supernatant of UL21-transfected cells | 1:100 | 3242 | 56.9 |
| supernatant of UL21-transfected cells | 1:500 | 4472 | 78.11 |
| supernatant of UL21-transfected cells | 1:2000 | 2526 | 46.79 |
| pellet of UL21-transfected cells | 1:20 | 3606 | 63.24 |

Example 4

Prevalence of Antigens in Population

This example supports the utility of preventative and therapeutic uses of the antigens of the invention by demonstrating the prevalence of responses to these antigens among the population. To do this, seven individuals who were HSV-2 infected as documented by type-specific serology were surveyed. These individuals were different from the individuals from whom the index T-cell clones were recovered from HSV-2 lesions.

For each subject, PBMC were isolated and plated at 2×10$^6$ cells/well in 2 mls of T-cell medium in 24-well plates and stimulated in vitro with a 1:500 dilution of UV-inactivated HSV-2 strain 333 for five days. At that time, 40 units/ml recombinant human IL-2 was added for an additional five to six days, giving rise to a short-term, HSV-specific cell line termed a B1 cell line.

Reactivity to individual HSV-2 proteins was assessed as follows. Proliferation assays were set up on 96-well round bottom microtiter plates, and each condition was performed in triplicate. To each well, 1×10$^5$ autologous irradiated (3300 rad gamma) PBMC were added as antigen presenting cells. To each well, 1×10$^4$ B1 cells were added. The following control substances were added: media, UV-treated mock virus preparation diluted 1:500, UV-treated HSV-2 strain 333 diluted 1:500, glycoproteins B or D or VP16 protein of HSV-2 (purified) at 4 micrograms per ml final concentration. The response to UV-treated HSV-2 was expected to be positive and served as a positive control for the viability and overall specificity of the cells. Glycoproteins B and D and VP16 were previously shown to be targets of HSV-specific T-cells (D. M. Koelle et al., 1994, J. Virol 68(5):2803–2810).

For the newly discovered antigens UL21, UL49, UL50, the cloning of the full-length genes and their expression in the eukaryotic Cos-7 system was as described above, as was the preparation of control antigens based on the empty vector. For the newly discovered antigen gE2 (US8), the full-length gene was cloned with high-fidelity thermostable DNA polymerase with proof-reading function from DNA prepared from HSV type 2 strain HG52 DNA using primers CGGGGTACCTGCTCGCGGGGCCGGGTTGGTG (SEQ ID NO: 10) at the 5' end of the gene and TGCTCTAGAGC-CTTACCAGCGGACGGACGG (SEQ ID NO: 11) at the 3' end of the gene. The PCR product was digested with ACC65 I and Xba I and cloned into similarly digested pcDNA3.1-myc-his-B (Invitrogen). The plasmid is named pcDNA3.1-myc-his-B-US8. The sequence was confirmed at the junctions between vector and insert. The predicted amino acid sequence of the expressed protein is identical to that predicted for viral US8. A N-terminal fusion domain derived from vector pcDNA3.1-myc-his- is also predicted to be expressed. To make eukaryotically expressed full-length US8 of HSV-2, the Cos-7 system was used as described above. For each of the four new antigens (UL21, UL49, UL50, and US8) and control, the supernatant and pellet after sonication of transfected Cos-7 cells was used at a final dilution of 1:20 in triplicate proliferation assays.

Positive responses were scored if the stimulation index (mean cpm $^3$H thymidine incorporation for test antigen/mean cpm $^3$H thymidine incorporation for relevant control antigen) was greater than or equal to 4.0. For UV HSV-2 antigen, the relevant control antigen was UV-mock virus. For gB2, gD2, and VP16, the control was media. For the new antigens expressed in Cos-7 cells, the control antigen was either the pellet or supernatant of Cos-7 cells transfected with control empty vector. Results are shown in Table 10. Reactivity with each of the newly discovered antigens was documented in at least one study subject. Overall, reactivity with UL49 was observed more frequently and similar to that for the known antigens gB2 and gD2. These data provide support that human individuals, in addition to the index subjects in whom the T-cell reactivity was originally described, are capable of reacting to these antigenic HSV-derived proteins.

TABLE 10

Antigenicity of known and of newly discovered HSV-2 antigens among a group of seven randomly chosen HSV-2 infected immunocompetent adults.

| | | | | ANTIGEN | | | | |
|---|---|---|---|---|---|---|---|---|
| | HSV-2 | gB2 | gD2 | VP16 of HSV-2 | UL49 of HSV-2 | UL50 of HSV-2 | UL21 of HSV-2 | US8 of HSV-2 |
| n | 7 | 5 | 5 | 0 | 5 | 1 | 1 | 2 |
| % | 100 | 71 | 71 | 0 | 71 | 14 | 14 | 28 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A pharmaceutical composition comprising an isolated HSV polypeptide and a pharmaceutically acceptable carrier, wherein the polypeptide comprises an amino acid sequence selected from the group consisting of: amino acids 18–312 and 118–250 of $U_L50$.

2. The composition of claim 1, wherein the polypeptide is a fusion protein.

3. The composition of claim 2, wherein the fusion protein is soluble.

4. The pharmaceutical composition of claim 1, further comprising an adjuvant.

5. A pharmaceutical composition comprising an isolated herpes simplex virus (HSV) polypeptide, wherein the polypeptide comprises a $U_L50$ protein, and a pharmaceutically acceptable carrier.

6. The composition of claim 5, wherein the polypeptide is a fusion protein.

7. The composition of claim 6, wherein the fusion protein is soluble.

8. The pharmaceutical composition of claim 5, further comprising an adjuvant.

9. A method of treating or preventing an HSV infection in a subject comprising administering the composition of claim 5 to the subject.

10. A method of enhancing proliferation of HSV-specific T cells comprising contacting the HSV-specific T cells with an isolated polypeptide that comprises a $U_L50$ polypeptide or immunogenic fragment thereof.

11. The method of claim 10, wherein the immunogenic fragment comprises amino acids 118–250 or 118–312 of $U_L50$.

12. A method of enhancing the production of HSV-specific antibodies in a subject comprising administering to the subject an isolated polypeptide that comprises a $U_L50$ polypeptide or immunogenic fragment thereof.

13. The method of claim 12, wherein the immunogenic fragment comprises amino acids 118–250 or 118–312 of $U_L50$.

14. A polynucleotide that encodes a polypeptide comprises an amino acid sequence consisting essentially of:

amino acids 118–312 or amino acids 118–250 of $U_L50$.

15. A vector comprising the polynucleotide of claim 14.

16. A host cell transformed with the vector of claim 15.

17. A method of producing an HSV polypeptide comprising culturing the host cell of claim 16 and recovering the polypeptide so produced.

18. An HSV polypeptide produced by culturing a host cell transformed with a vector comprising a polynucleotide encoding an HSV $U_L50$ polypeptide wherein the HSV $U_L50$ polypeptide consists essentially of amino acids 118–250 or 118–312 of $U_L50$.

19. A recombinant virus genetically modified to express the polypeptide of claim 18.

20. A fusion protein comprising an HSV polypeptide fused to a heterologous polypeptide, wherein the HSV polypeptide consists essentially of amino acids 118–250 or 118–312 of $U_L50$.

21. A fusion of claim 20 that is soluble.

22. A polynucleotide that encodes a fusion protein of claim 20.

23. A vector comprising the polynucleotide of claim 22.

24. A host cell transformed with the vector of claim 23.

25. A method of producing a fusion protein comprising culturing the host cell of claim 24 and recovering the fusion protein so produced.

26. A fusion protein produced by the method of claim 25.

27. A fusion protein of claim 26 that is soluble.

28. A pharmaceutical composition comprising the fusion protein of claim 26, and a pharmaceutically acceptable carrier.

29. The pharmaceutical composition of claim 28, further comprising adjuvant.

30. A pharmaceutical composition comprising the fusion protein of claim 20, and a pharmaceutical acceptable carrier.

31. The pharmaceutical composition of claim 30, further comprising an adjuvant.

32. A recombinant virus genetically modified to express a $U_L50$ protein wherein the protein consists essentially of amino acids 118–250 or 118–312 of $U_L50$.

33. The recombinant virus of claim 32 which is a vaccinia virus, canary pox virus, lentivirus, retrovirus, herpes virus or adenovirus.

34. A pharmaceutical composition comprising the virus of claim 33 and a pharmaceutically acceptable carrier, wherein the virus is a vaccininia virus or acanary pox virus.

35. The pharmaceutical composition of claim 34, further comprising an adjuvant.

36. A recombinant non-HSV virus genetically modified to express a $U_L50$ protein.

37. A recombinant non-HSV virus of claim 36 which is a vaccinia virus, canary pox virus, lentivirus, retrovirus, herpes virus or adenovirus.

38. A pharmaceutical composition comprising the non-HSV virus of claim 36 and a pharmaceutically acceptable carrier, wherein the virus is a vaccinia virus or a canary pox virus.

39. The pharmaceutical composition of claim 38, further comprising an adjuvant.

* * * * *

UNITED STATES PATENT AND TRADEMARK OFFICE
CERTIFICATE OF CORRECTION

PATENT NO.    : 6,375,952 B1                                    Page 1 of 1
DATED         : April 23, 2002
INVENTOR(S)   : David M. Koelle and Lawrence Corey It is certified that error appears in the above-identified patent and that said Letters Patent is hereby corrected as shown below:

<u>Title page,</u>
Item [56], References Cited, OTHER PUBLICATIONS, please add:
-- Paoletti, Proceedings of the National Academy of Science USA 93:11349-11353, October 1996 --

Signed and Sealed this

Twenty-ninth Day of April, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,375,952 B1 | |
| APPLICATION NO. | : 09/368770 | |
| DATED | : April 23, 2002 | |
| INVENTOR(S) | : Koelle et al. | |

It is certified that error appears in the above-identified patent and that said Letters Patent is hereby corrected as shown below:

Column 1, lines 9-12,

Please delete the paragraph that reads:

"The invention disclosed herein was made with Government support under Grant No. AI34616, awarded by the National Institutes of Hearth. The government has certain rights in this invention."

and insert:

--This invention was made with government support under grant numbers AI34616 and AI30731 awarded by National Institutes of Health. The government has certain rights in the invention.--

Signed and Sealed this
Eighth Day of March, 2011

David J. Kappos
*Director of the United States Patent and Trademark Office*